United States Patent
Butterfield et al.

(10) Patent No.: US 6,416,291 B1
(45) Date of Patent: *Jul. 9, 2002

(54) FLUID FLOW RESISTANCE MONITORING SYSTEM

(75) Inventors: Robert D. Butterfield, Poway; Allen B. Farquhar, San Diego, both of CA (US)

(73) Assignee: Alaris Medical Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/602,831

(22) Filed: Jun. 23, 2000

Related U.S. Application Data

(63) Continuation of application No. 08/688,673, filed on Jul. 30, 1996.

(51) Int. Cl.[7] .......................... F04B 49/06; F04B 49/00; A61M 31/00; A61M 5/00
(52) U.S. Cl. .......................... 417/44.2; 417/38; 604/67; 604/9
(58) Field of Search ............................... 417/9, 20, 22, 417/29, 31, 38, 43, 44.2, 477.1, 477.3, 477.6, 477.13; 604/9, 50

(56) References Cited

U.S. PATENT DOCUMENTS

| | | | |
|---|---|---|---|
| 4,979,940 A | * 12/1990 | Bobo, Jr. et al. | 604/50 |
| 5,087,245 A | * 2/1992 | Doan | 604/67 |
| 5,423,743 A | * 6/1995 | Butterfield | 604/50 |
| 5,803,917 A | * 9/1998 | Butterfield et al. | 604/67 |
| 6,158,965 A | * 12/2000 | Butterfield et al. | 417/44.2 |

* cited by examiner

Primary Examiner—Charles G. Freay
Assistant Examiner—Michael K. Gray
(74) Attorney, Agent, or Firm—Fulwider Patton Lee & Utecht, LLP

(57) ABSTRACT

Flow parameters in a fluid delivery assembly are determined by monitoring pressure responses and processing those responses along with information regarding the fluid flow. In one aspect, a processor controls the pump to pump flow quantities in accordance with a pseudorandom code. Portions of the resulting pressure signal sensed at the conduit is averaged, and the averaged values are then decoded in accordance with the pseudorandom code. An estimate of the equilibrium pressure is generated from the decoded average pressure values, while a summation of the pressure samples is generated from the undecoded pressure signals. The resistance to fluid flow of the system is determined from the estimated equilibrium pressure and pressure summation. For low flow rates, a processor controls the pump to pump fluid in a series of fluid boluses, with each fluid bolus delivered in the beginning of a separate timeslot. The equilibrium pressure is measured at the end of each timeslot, and a summation of the pressure samples is generated from the pressure signals. For high flow rates, the pump is controlled to vary the flow rate and the change in pressure is divided by the change in flow to directly determine the resistance. A resistance display continuously displays the resistance of the system. The pseudorandom coding and decoding can be used to filter out pressure-response crosstalk caused by multiple fluid infusion segments feeding into a common line.

23 Claims, 15 Drawing Sheets

Cbit

X + X + X = (+2) + (+3) + (−1) = DECODE (0) = 4

BLSA

Cbit

X + X + X = (−2) + (+3) + (+1) = DECODE (1) = 2

BLSA

Cbit

X + X + X = (+2) + (−3) + (+1) = DECODE (2) = 0

BLSA

FLUID FLOW RESISTANCE MONITORING SYSTEM

This application is a continuation of Ser. No. 08/688,673 filed Jul. 30, 1996.

BACKGROUND OF THE INVENTION

1. Field of the Invention

The invention relates to fluid delivery systems. More particularly, the present invention relates to monitoring the resistance to fluid flow in a fluid delivery system infusing fluid to a patient.

2. Description of Related Art

There are a variety of situations where fluid is infused to a patient. Applications of fluid delivery systems include (but are by no means limited to) intravenous infusion, intra-arterial infusion, infusion of enteral solutions, infusion of medication to the epidural space, and diagnostic infusion to determine vascular characteristics of the arterial, urinary, lymphatic, or cerebrospinal systems.

Fluid delivery systems for infusing fluid to a patient typically include a supply of the fluid to be administered, an infusion needle or cannula, an administration set connecting the fluid supply to the cannula, and a flow control device, such as a positive displacement infusion pump. The administration set typically comprises a length of flexible tubing. The cannula is mounted at the distal end of the flexible tubing for insertion into a patient's blood vessel or other body location to deliver the fluid infusate to the patient. The flow control device often is a peristaltic-type pump that acts on the flexible tubing to force the fluid through the tubing of the administration set to the cannula and into the patient. One commonly used flow control device is a linear peristaltic type pump having several cams and cam-actuated fingers that sequentially occlude portions of the flexible tubing along a pumping zone to create a moving zone of occlusion.

During an infusion procedure, events may occur that interfere with proper delivery of fluid to the patient, such as an occlusion of the administration line. It is desirable to detect these events as soon as possible so that they can be remedied.

A common technique for detecting such events and for evaluating fluid delivery system status is to monitor the pressure in the administration set. Variations in pressure can indicate problems with fluid delivery. For example, an increase in pressure over a selected threshold may indicate an occlusion in the system. Similarly, a drop in pressure can indicate an empty fluid supply or other fluid delivery system fault.

A problem with determining fluid delivery system status by monitoring pressure alone is the slow speed at which pressure can build when the system is operating at a low flow rate. At low flow rates, the energy per unit time introduced into the flow path is very small. Accordingly, it may take a considerable amount of time for the pressure to build up enough to exceed a threshold and indicate an occlusion. Additionally, with a relatively low pressure threshold, patient movements such as coughing, sneezing, and sitting up can cause the pressure to momentarily exceed the pressure threshold, thus creating a false alarm of a fluid delivery system fault. Another problem with monitoring pressure alone occurs when the delivery cannula becomes mislocated within the interstitial tissue matrix, causing a rise in pressure. The amount of resulting pressure rise is dependent upon flow rate. For example, at a flow rate of 10 ml/hr, the rise in pressure is typically only about 10 mm Hg; at a flow rate of 2 ml/hr, the rise in pressure is typically only about 2 mm Hg. Such small relative changes are difficult to detect from instantaneous pressure readouts, or even from pressure trends, because of the presence of other sources of change, such as patient movement, as well as venous pressure, elevation of the system components, and the flow rate itself.

As has been noted in U.S. Pat. No. 4,898,576 to Philip, the measure of the resistive part of the fluid line impedance can be used to monitor the condition of the fluid line. One technique used in actively monitoring the resistance, rather than merely waiting for pressure to build up, is the alteration of the flow rate. The change in the pressure over the change in the flow rate has been found to accurately indicate the resistive part of the fluid impedance in the system when adequate time is allowed for the pressure to reach equilibrium at each rate. This technique has been found to be effective at higher flow rates with their accompanying higher pressures. A change in these higher flow rates is accompanied by a rapid and measurable change in pressure. Because of the rapid pressure response to the flow rate changes, the flow rate can be varied about the selected flow rate without any significant clinical effect on flow uniformity.

However, at lower flow rates, the clinical requirement of flow rate uniformity restricts the magnitude of the changes to the flow that can be imposed on the fluid line. It is thus undesirable to alternate between different flow rates to obtain different pressure responses for determining resistance due to the detrimental effect on flow uniformity the flow changes would have as well as the relatively long length of time required to obtain those pressure responses.

Various models of pressure and resistance can allow accurate resistance measurements. For example, as described in U.S. Pat. No. 5,087,245 to Doan, which is incorporated herein by reference, a technique for determining flow resistance which allows for a non-linear relation between pressure and flow and a time-varying impedance (resistance and compliance) involves inducing a bolus of fluid in the infusion system and monitoring the resulting pressure wave and the pressure decay response. Injecting a known quantity of fluid causes a resulting pressure wave that then decays to an equilibrium pressure. Using the equilibrium pressure and the pressure decay response, fluid resistance can then be determined even when a non-linear relation between flow and pressure exists and when the impedance (resistance and compliance) are time-varying via the following equation:

$$\text{Resistance} = \frac{A_p}{A_f} = \frac{\int (P(t) - P_0)dt}{\int F(t)dt}$$

where: $\int F(t)\,dt = Q =$ the known delivered quantity of fluid,

P(t)=the change in pressure over time, $P_o$=the equilibrium or offset pressure, $A_p$=the area under a pressure response waveform, and $A_f$=the area under a fluid flow waveform.

Thus, by injecting a known quantity of fluid through the infusion system, monitoring the resulting pressure as it decays to an equilibrium pressure, and determining an integral of the difference between the equilibrium pressure and the pressure response, the resistance to fluid flow can be determined. However, after the known quantity of fluid is injected, further quantities of fluid can not be injected through the system (i.e., further flow steps are not initiated) in order for the pressure to decay to the equilibrium pressure. In some situations, such as where the fluid resistance is relatively high, a relatively long pause in fluid injection may be necessary to allow the pressure to reach equilibrium pressure. Depending on the particular application, such long delays between fluid flow steps may be undesirable.

As set forth in pending U.S. patent application Ser. No. 08/305,904, pseudo-random binary sequence (PRBS) codes have been used to effectively eliminate the delays in reaching equilibrium pressure by creating "virtual" waveforms. However, due to the high processing requirements of PRBS coding and decoding procedures, PRBS codes have only been used in combination with linear and non-time-variant models of pressure and resistance, such as the following equation:

$$P(t) = Resistance * F(t) + \frac{\int F(t)}{Compliance}$$

Where F=Flow rate,
P=Pressure, and
Resistance and Compliance are stationary values (i.e., values that do not vary with time or flow).

Such a linear and non-time variant estimation technique is relatively accurate over fluid resistances between 0 to 1500 fluid ohms (where 1 fluid ohm=1 mm Hg per liter per hour). However, because fluid impedance (i.e., resistance and compliance) is in actuality time-variant and non-linear, the above-cited estimation technique has reduced accuracy where the fluid resistance exceeds 1500 fluid ohms.

Note that fluid resistance is a part of the total system fluid impedance. Fluid impedance is a function of the system compliance, inertance, and resistance.

The causes of the non-linear, time-variant resistance relationship include the viscoelasticity of the flexible tubing, which slowly contracts following application of a positive pressure transient. Additionally, the biochemical and rheological aspects of the patient's fluid system, such as the blood flow in the human body, further complicate the pressure/flow relationship.

There are several applications of parenteral infusion systems where both low flow rates and high resistances are encountered. For example, infusing parenteral liquids into small children and infants, and particularly into premature infants, can involve low flow rates and high resistances.

An additional problem with monitoring fluid infusion systems is caused by various "noise" sources that can degrade the pressure monitoring. Such noise sources include movement of the fluid infusion system and patient movement such as breathing and ambulation. Additionally, using more than one pump and administration set to inject fluid through a single fluid delivery system cannula can introduce noise that can interfere with individually monitoring the flow in the various administration sets.

Hence, those skilled in the art have recognized a need for a fluid delivery monitoring system that can detect a fluid delivery fault condition faster and with improved specificity than prior systems at low flow rates. There is also a recognized need for a system that can compensate for the existence of offset pressure while maintaining clinically acceptable flow patterns, and that can detect partial or "soft" occlusions that may result in pressure changes that are too small to be noticed through conventional pressure monitoring systems. Additionally, it has also been recognized that there is a need for a system that is less sensitive to other sources of pressure changes in the conduit such as those caused by other pumps on the same fluid line. It is further desirable to have a system that is accurate over a wide range of resistances and that is less sensitive to noise effects. The present invention satisfies these needs and others.

SUMMARY OF THE INVENTION

Briefly and in general terms, the present invention is directed to a system that monitors one or more flow parameters in a fluid delivery assembly. In a fluid delivery system in which a flow control device acts on a fluid conduit to control the movement of fluid through the conduit, the system for monitoring one or more flow parameters comprises a pressure sensor coupled to the conduit for providing pressure signals in response to the pressure sensed in the conduit, and a processor that receives the pressure signals, processes those pressure signals, and determines a flow parameter based on said processing.

In one more detailed aspect, the processor determines flow resistance.

In a further aspect, the processor controls the flow control device to cause various flow rates to exist in the conduit, with the application of specific flow rates dependent upon whether the selected flow rate is high, medium, or low. The processor applies different resistance measurement techniques depending on the selected flow rate.

In a further aspect, a pseudorandom code is used to create a repeating, non-uniform flow pattern, which induces pressure responses which are measured, averaged, and then decoded to compute the estimated equilibrium pressure or total offset pressure. The pressure responses over a pseudo-random code period are also summed. The pressure response summation and the estimated equilibrium pressure are then used to determine the flow resistance.

In yet another aspect, where the selected flow rate falls below a low threshold, the processor determines a timeslot length and controls the flow control device to deliver a bolus of fluid at the beginning of the timeslot. The pressure response is monitored to determine an equilibrium pressure, and the sum of the pressure response is determined. The resistance is calculated using the determined equilibrium pressure and the pressure response sum.

In a further more detailed aspect, where the selected flow rate exceeds a high threshold, the processor controls the flow control device to cause a plurality of different flow rates to exist in the conduit. The processor then processes the difference in the pressures and the difference in the flow rates to determine the impedance to flow.

In yet a further aspect, the processor controls the flow control device to deliver a closely spaced series, or "trill", of flow waveforms at the beginning of a timeslot.

In another aspect that may be used with a fluid delivery system that includes two or more fluid infusion segments, each of which may include a separate fluid source and a separate flow control device acting on a separate fluid line; each of the two or more fluid infusion segments feeds into common fluid line that delivers fluid to a patient; and where at least one of the fluid infusion segments includes a processor that controls the flow control device, the processor uses a pseudorandom coding and decoding process to filter pressure-response crosstalk caused by the other fluid infusion segments.

In another more detailed aspect of the invention, the system determines an estimate of signal quality and noise.

Other features and advantages of the present invention will become more apparent from the following detailed

DETAILED DESCRIPTION OF THE PREFERRED EMBODIMENTS

Figure 1:
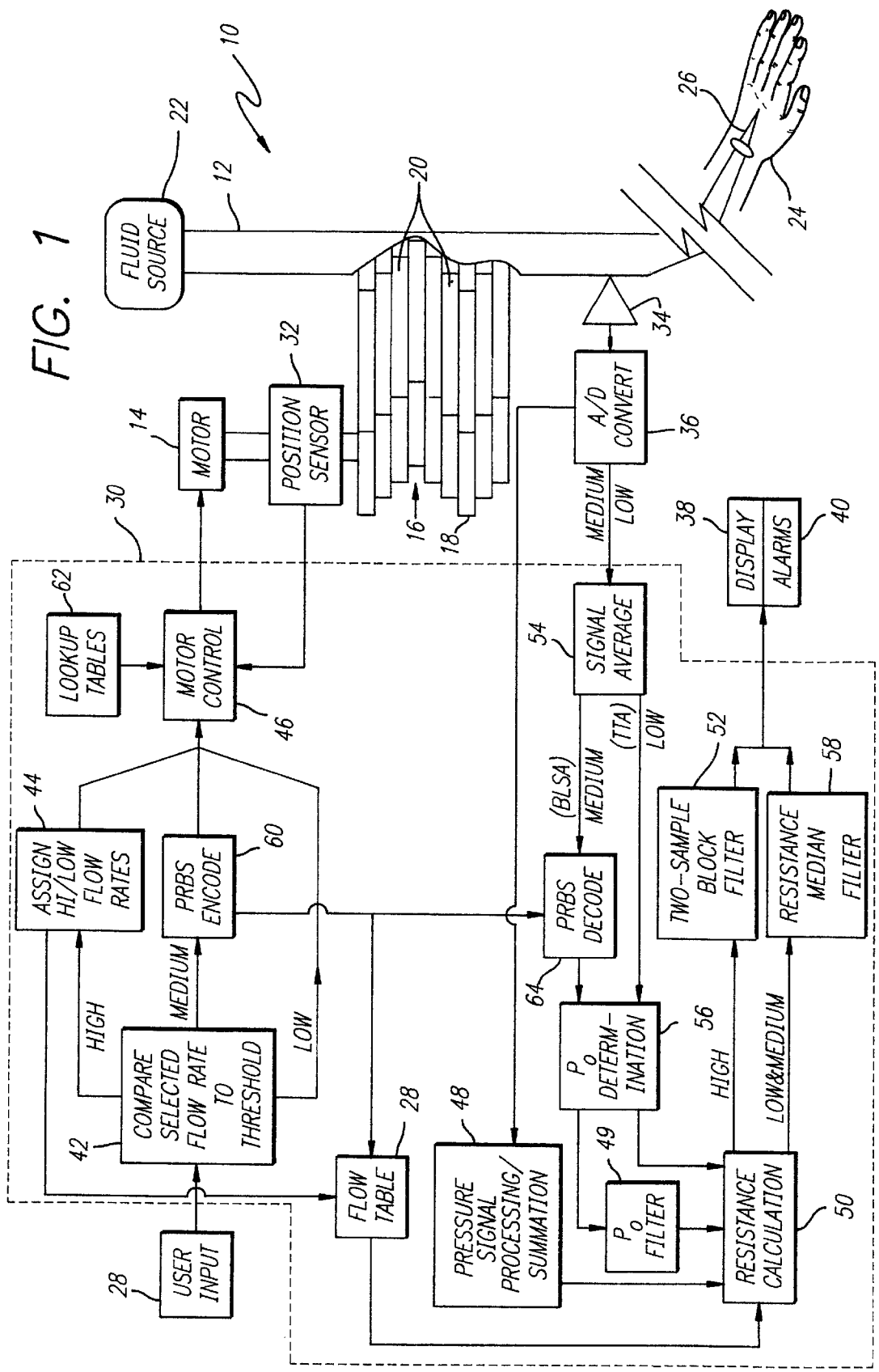
FIG. 1 is a simplified block diagram of a system for detecting abnormalities in a fluid line incorporating the principles of the invention as applied to an intravascular fluid infusion system.

Referring now to the drawings with more particularity, wherein like reference numerals in the separate views indicate like or corresponding elements, there is shown in FIG. 1 a block diagram of a resistance monitoring system 10 incorporating aspects of the current invention. The resistance monitoring system is coupled to the conduit 12 of a fluid delivery system in which a pump motor 14 drives a pumping mechanism 16, which in the embodiment shown comprises a rotating cam shaft 18 coupled to the pump motor 14 and moving a series of peristaltic elements 20. The peristaltic elements 20 operate on the conduit 12 to move fluid from a fluid source 22, through the conduit 12, and into a patient 24 via a cannula 26.

A user input device 28, such as a keypad, provides operator instructions, such as flow rate selection, to a processor 30. The processor 30 controls the operation of the pump motor 14 driving the pumping mechanism 16. A motor position sensor 32 determines the position of the motor 14 and pumping mechanism 16 and provides a position signal to the processor 30.

Located downstream from the pumping mechanism is a pressure sensor 34 coupled to the conduit 12 to sense pressure in the conduit. An analog-to-digital converter 36 ("A-to-D") receives the analog pressure output signals from the sensor 34 and converts them to a digital format at a particular sample rate controlled by the processor 30. The processor 30 receives the digital pressure signals, processes them as described in more detail below and calculates the resistance to flow. A display 38 presents the resistance. One or more alarms 40 are provided to indicate an unsatisfactory resistance level. As a backup to the resistance monitoring system, the alarm system 40 may also be activated when the pressure exceeds a set threshold. Where such a backup system is present, the processor 30 compares monitored pressure values against a pressure threshold. If the monitored pressure (or, to prevent false alarms, an average of several recent monitored pressure values) exceeds the pressure threshold, the alarm system 40 will be activated. Such a pressure threshold will typically be relatively high to prevent false alarms. In a preferred embodiment, the pressure threshold is 600 mm Hg.

The selection of a flow rate is made at the keypad 28 and is received by the processor 30. The user may also select at the keypad 28 a high or a low resistance range. In one embodiment, the high range is from 0 to 2000 fluid ohms, and the high range is from 0 to 6000 fluid ohms. The selection of range is used to drive the display and alarm systems, as well as to determine resistance percent (as set forth below regarding equation 4). The user selects the high or low resistance depending on the particular application.

In a preferred embodiment, the processor 30, after receiving the selected flow rate from the user input 28, compares 42 the selected flow rate against flow rate thresholds to determine if the selection is a "high" flow rate, "medium" flow rate, or a "low" flow rate. Two thresholds, one low and one high, are used to divide the high, medium, and low flow rates. A selected flow rate exceeding the high threshold is considered high, a selected flow rate falling below the low threshold is considered low, and a selected flow rate between the thresholds is considered a medium threshold. In a preferred embodiment, the low threshold is 0.5 milliliters per hour, and the high flow rate is 50 milliliters per hour.

As one aspect of the resistance monitoring system shown in FIG. 1, three different approaches to determining the fluid system resistance are used so that a wide range of flow rates and resistances may be provided by the fluid delivery system with continuous, accurate resistance determination.

For high flow rates, a bi-rate approach is used, whereby the processor 30 selects 44 two or more different flow rates at which the motor will run. The flow rate commands are provided to the motor controller 46 which in turn causes the pump motor 14 to act on the conduit 12 through the pump mechanism 16 to pump fluid through the conduit 12 at those discrete rates. The rates are selected in one embodiment to average to the selected flow rate for the purpose of maintaining flow uniformity.

The pressure responses to the flow waveforms in the conduit 12 are monitored by the pressure sensor 34 with digital pressure signals provided to the processor 30 by the A-to-D converter 36. Those pressure signals are processed 48, which for the high rate involves full pump revolution averages for the last revolution in each bi-rate range. The output is then used with flow table information 28 to calculate 50 the fluid resistance. The calculated resistance may be filtered 52, such as through a moving average or moving median filter, to improve the accuracy of the resistance calculation. The filtered resistance is shown in the display 38 and sent to the alarm system 40.

Varying the flow rate at relatively high flow rates causes a large and rapid pressure response as discussed above, and the resistance to fluid flow of the system can be determined relatively rapidly in accordance with the following:

$$R = \frac{P_2 - P_1}{F_2 - F_1}$$

where: R=resistance
$F_1$=first flow rate
$F_2$=second flow rate
$P_1$=pressure at the first flow rate
$P_2$=pressure at the second flow rate Another relationship that may be used in determining a resistance percentage and that takes into account the sample rate is:

$$R\% = (SCALE) \frac{\frac{\sum_{j=0}^{M-1} p_{hi}(j)}{M} - \frac{\sum_{k=0}^{N-1} p_{lo}(k)}{N}}{F_{hi} - F_{lo}}$$

where: R%=resistance in percent;
SCALE=a scale factor, equal to ($\frac{1}{20}$), or (100/(2000 fluid ohms)), for a low user-selected resistance scale of 0 to 2000 fluid ohms, and equal to ($\frac{1}{60}$), or (100/(6000 fluid ohms)), for a high user-selected resistance scale of 0 to 6000 fluid ohms;
P=pressure in mm Hg;
F=flow in liters per hour;
M=samples in one revolution at the high rate; and
N=samples in one revolution at the low rate.

Therefore, for high flow rates (which in the embodiment shown are above 50 ml/hr), a "bi-rate" approach is used where the flow rate is varied at two or more flow rates about the selected flow rate. The responsive pressure signals are monitored. In this approach, the changes in pressure resulting from the flow rates are used to directly calculate resistance. The flow rates selected and the length of time that they are each applied are based on averaging to the selected flow rate, so that there is no significant clinical effect by altering the flow rates.

Further details regarding determination of fluid resistance at high flow rates using the above-cited high-low flow rate technique are discussed in detail in pending U.S. patent application Ser. No. 08/305,904, which is incorporated herein by reference.

Figure 2A:
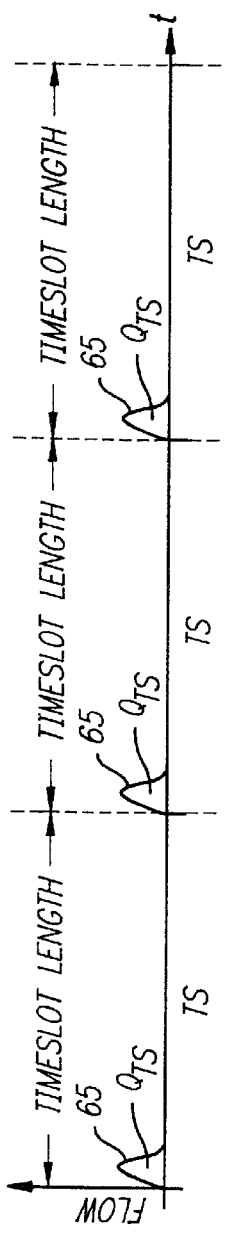
FIGS. 2(A), 2(B), 2(C) and 2(D) are a graphical representations of fluid flow and corresponding pressure responses.
Figure 2B:
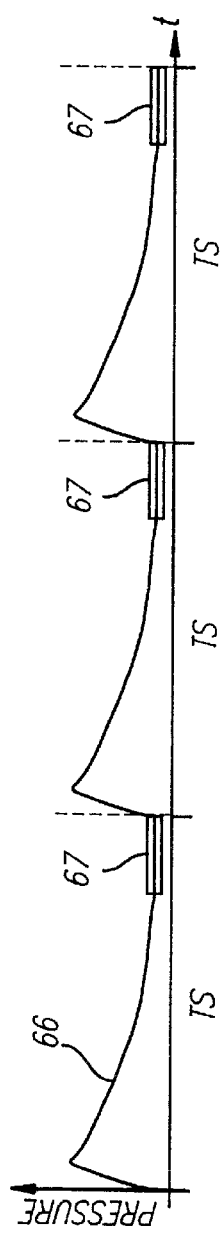

For low flow rates, which in one embodiment are flow rates below 0.5 ml/hour, resistance determination is performed using a second technique. The drive controller does not use PRBS encoding. Instead, the user selected flow rate is used by the motor controller 46 to divide the pump cycle into a number of timeslots TS, with all timeslots of equal length, as shown in FIG. 2a. Timeslot length is maximized, and the motor is controlled to deliver a fluid volume $Q_{TS}$ in each timeslot, preferably as a single bolus 65 toward the beginning of the timeslot. The resulting pressure waveform 66 is shown in FIG. 2b. By maximizing timeslot length, sufficient time is permitted for the pressure in the conduit to decay to the equilibrium pressure $P_o$, which, to reduce the impact of noise and other spurious signals, can be calculated as the average of the last portion 67 (i.e., the "tail") of the waveform in a particular timeslot.

Referring again to FIG. 1, the pressure is monitored by the sensor 34, the pressure signals are A/D converted 36, and the tail portion of the pressure signals from a timeslot is used to calculate a signal average 54, such as a Timeslot Tail Average (TTA). The TTA value is used to determine $P_o$ 56. The A/D converted pressure signals are also sent to signal processing to generate a summation of the pressure signal values. The pressure summation and $P_o$ value are used to calculate the resistance 50. The resistance value may be filtered 58 to increase accuracy and remove noise effects. The filtered resistance value is then provided to the display 38 and alarm system 40.

For medium flow rates, which in one embodiment are flow rates between 0.5 ml/hr and 50 ml/hr, the actual flow rate is varied about the selected flow rate in accordance with a pseudorandom pattern of variation about the selected rate. The pseudorandom pattern is provided by a pseudorandom encoder, which in the embodiment shown is a PseudoRandom Binary Sequence (PRBS) encoder 60, the operation of which is discussed in greater detail with respect to FIG. 7. The PRBS code is provided to the motor control 46, which uses volume data (from lookup tables 62), the PRBS code, and the user-selected flow rate to determine a desired repeating, non-uniform flow pattern, as discussed in greater detail below with respect to FIGS. 6 and 7. The motor control 46 also divides the pump cycle into a number of timeslots TS. The motor control 46 then causes the pump motor 14 to act on the conduit 12 through the pump mechanism 16 to pump fluid through the conduit 12 at the determined repeating, non-uniform flow pattern.

Figure 2C:
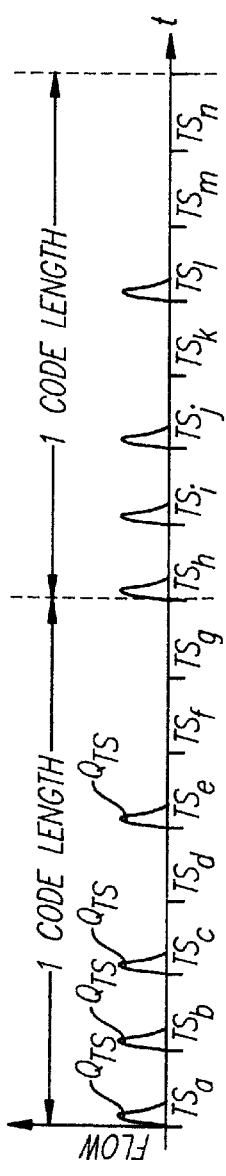
Figure 2D:
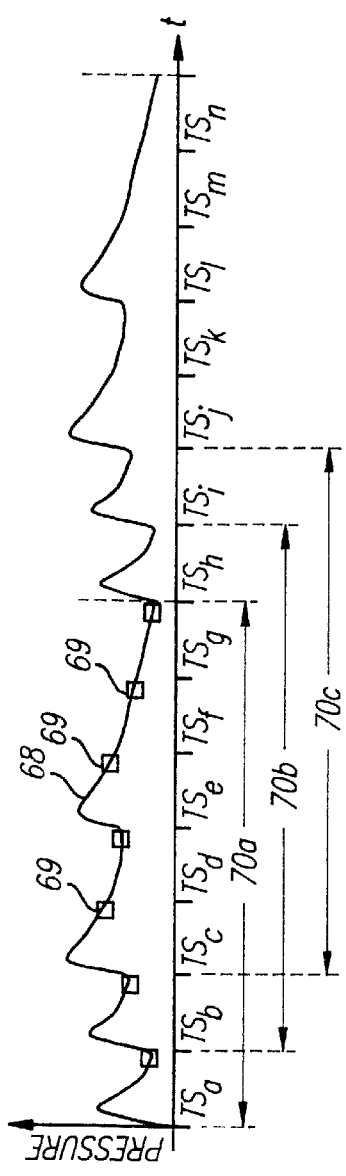

FIGS. 2c and 2d show sample flow and pressure waveforms from a PRBS code. In the example of FIG. 2c, a PRBS code of length 7 and having elements of 1 1 1 0 1 0 0 is used to control fluid infusion. One element (i.e., a 1 or a 0) of the PRBS code is assigned to each timeslot. For each timeslot having a corresponding PRBS element of 1, a single small fluid bolus of volume $Q_{TS}$ is injected, as shown in FIG. 2c, preferably at the beginning of the timeslot. The resulting pressure waveform 68 is shown in FIG. 2d.

Referring again to FIG. 1, for medium flow rates, the resulting pressure in the conduit 12 is monitored by a pressure sensor 34 that outputs pressure signals. All or some of the pressure signals are averaged 54 to create average pressure values, such as BaseLine Sample Averages (BLSAs). A Baseline Sample Average is an average of a portion of the pressure signals in a timeslot, such as the tail portions 69 depicted in FIG. 2d.

Referring again to FIG. 1, the BLSAs are decoded 64 in accordance with the pseudorandom pattern of variation, and the decoded average pressure values are used for estimated equilibrium pressure ($P_o$) determination 56.

Note that pressure signal averaging 54 is included to decrease the processing requirements for decoding and to eliminate noise/spurious signals. The system could also operate by decoding the pressure signals without any averaging. However, decoding is processor-intensive, as set forth below with respect to FIG. 9. Accordingly, decoding all the pressure signals, instead of just average pressure values, could substantially increase the processing requirements.

The calculated $P_o$ values may be filtered 49, such as through the median filter process described below with respect to FIG. 11, in order to reduce noise effects and increase the accuracy of the $P_o$ value. The filtered $P_o$ value is provided for resistance calculation 50.

The A/D converted pressure signals are processed 48 to provide a pressure summation value. The pressure summation value and filtered equilibrium pressure $P_o$ are then used to calculate the resistance 50. The calculated resistance may be filtered 58, such as through the median filter process described below with respect to FIG. 11, in order to increase the accuracy of the resistance value. The filtered resistance is provided to the display 38 and alarm system 40.

Note that the $P_o$ and resistance values can be updated with each new timeslot, and does not require an entirely new PRBS code cycle to be completed. For example, as shown in FIG. 2d, updated $P_o$ and resistance values can be determined over the range 70a, which encompasses the first M timeslots shown ($TS_a$ through $TS_g$, where codelength M=7). Upon receiving data from another timeslot, such as $TS_h$, updated $P_o$ and resistance values can be determined over the new range 70b, which encompasses timeslots $TS_b$ through $TS_h$. Upon receiving data from still another timeslot, such as $TS_i$, updated $P_o$ and resistance values can be determined over the new range 70c, which encompasses timeslots $TS_c$ through $TS_i$. Thus, even though M timeslots are used to determine $P_o$ and resistance, the system does not have to wait M timeslots for an updated calculation of $P_o$ and resistance. Instead, each time new pressure date is received for a new timeslot, an updated calculation of $P_o$ and resistance calculation is performed using data from the new timeslot and the most recent (M−1) timeslots.

Figure 3:
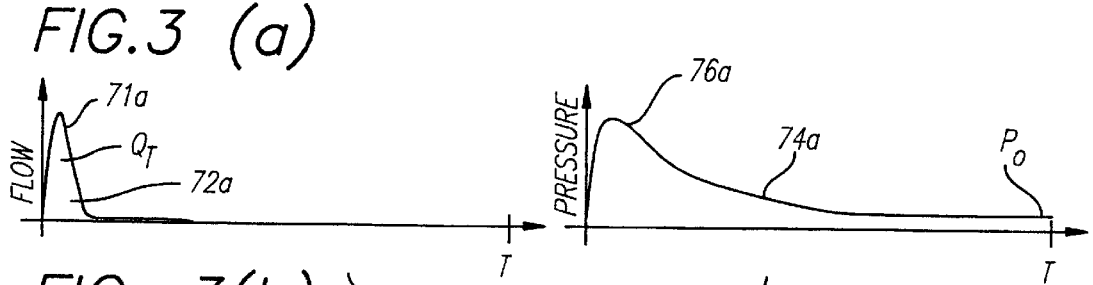
FIGS. 3(a), 3(b), 3(c), 3(d), 3(e) and 3(f) are graphical representations of different fluid flow waveforms and corresponding pressure responses.

The rationale for using the pseudorandom pattern is outlined in FIG. 3, which shows various flow waveforms and their corresponding pressure waveforms. In FIG. 3a, an induced flow waveform 71a comprises a single bolus of fluid 72a injected at the beginning of a time period T. The bolus 72a has a volume $Q_T$. The resulting pressure waveform 74a has an initial peak $76_a$ that decays to an equilibrium pressure $P_o$ at or near the end of the time period T. The equilibrium pressure can be used to accurately determine the flow resistance in the fluid delivery system. However, waiting for the pressure to decay to the equilibrium pressure can take a long period of time, such as a minute or more.

Figure 3B:
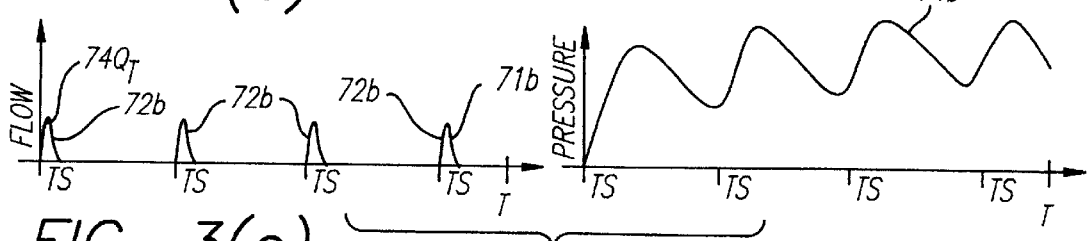

In many circumstances, the settling time required for the pressure to decay to the equilibrium pressure is too long for practical use in intravenous fluid delivery systems. Additionally, delivering a large, single bolus of fluid can be undesirable. It is often preferable to deliver a series of smaller boluses 72b of fluid equally spaced over the time period T, as depicted in the flow waveform 71b in FIG. 3b. However, such equally spaced small boluses 72b can result in a pressure waveform 74b such as that shown in FIG. 3b, where there is insufficient time between flow boluses 72b for the pressure to decay to the equilibrium pressure. In such a case, the equilibrium pressure cannot be directly measured.

In one aspect of the current invention, a series of small boluses of fluid are delivered over the time period T, with the small boluses spaced over a number M of timeslots using a pseudorandom code whose length M equals the number of timeslots into which the period T is divided. In the example shown in FIG. 3c, The pseudorandom sequence is a PseudoRandom Binary Sequence (PRBS) whose length M equals 7. The PRBS code shown is 1 1 1 0 1 0 0, where 1 indicates a bolus of fluid delivered in the particular timeslot TS, and 0 indicates that no bolus of fluid is delivered in that timeslot TS.

Figure 3C:
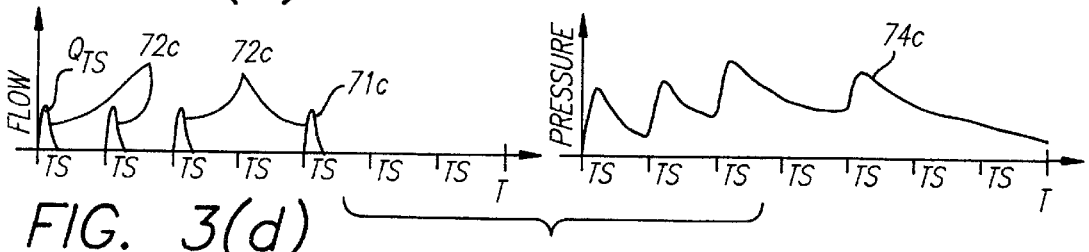
Figure 3D:
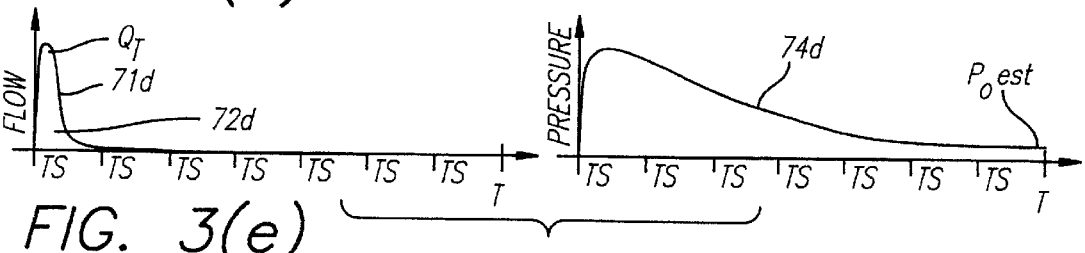

As shown in FIG. 3c, the pressure waveform 74c resulting from the PRBS-coded fluid delivery shows that there is not sufficient time between boluses 72c for the pressure waveform 74c to decay to an equilibrium pressure. Accordingly, the equilibrium pressure cannot be directly measured. However, by decoding the entire pressure waveform of FIG. 3c using the same PRBS code (1110100) in a decoding process, an estimated pressure waveform 74d can be generated, as shown in FIG. 3d. The estimated pressure waveform 74d corresponds to a virtual single bolus of fluid 72d delivered at the beginning of the time period T. Moreover, the final portion of the estimated pressure waveform 74d provides a close approximation $P_o$est of the equilibrium pressure $P_o$ that would have actually occurred if sufficient time were allowed between flow boluses for the pressure to properly decay.

Accordingly, even though the actual delivered flow and the actual measured pressure follow the waveforms 71c, 74c set forth in FIG. 3c, by decoding the measured pressure waveform 74c with the PRBS code, a "virtual" pressure waveform 74d such as that set forth in FIG. 3d can be calculated, with the "virtual" pressure waveform 74d corresponding to the pressure waveform 74a from FIG. 3a that is desired for $P_o$ determination purposes.

Figure 3E:
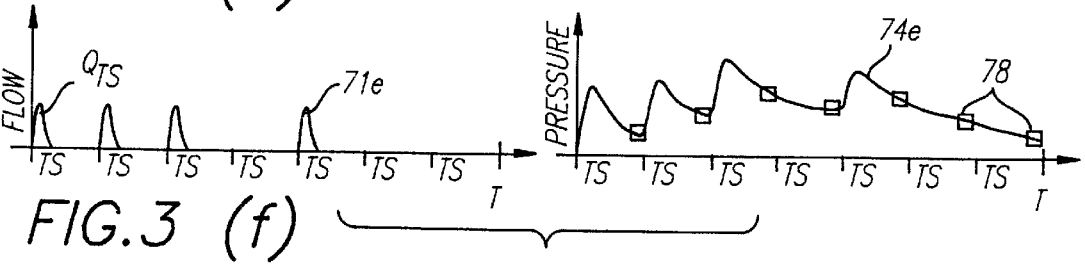
Figure 3:
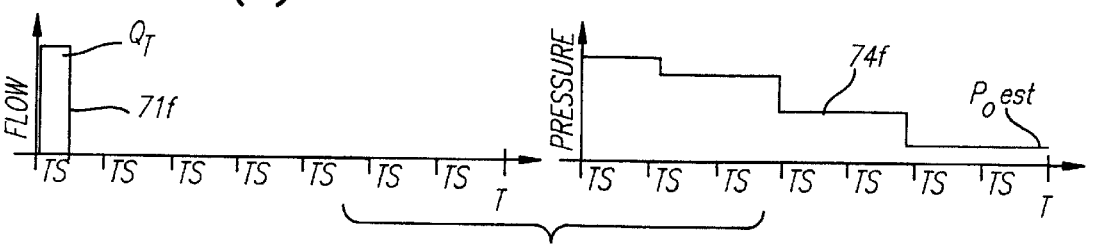

However, decoding the entire pressure waveform, or even substantial portions thereof, requires decoding hundreds of individual pressure signals. Because decoding is a processor-intensive procedure, it is desirable to reduce the number of signals decoded. It has been found that by taking an average pressure value 78 from each timeslot TS, as shown in FIG. 3e, and decoding just one average pressure value for each timeslot, the resulting estimated pressure waveform 74f, shown in FIG. 3f, can be used to determine equilibrium pressure, and the resulting estimated equilibrium pressure $P_o$est is a close approximation of the estimated equilibrium pressure that would have been generated by decoding all of the pressure signals without averaging.

Accordingly, even though the actual delivered flow and the actual measured pressure follow the waveforms 71c, 74c set forth in FIG. 3c, by averaging the pressure signals and then decoding the averaged pressure values with the PRBS code, a "virtual" pressure waveform 74f such as that set forth in FIG. 3f can be calculated, with the "virtual" pressure waveform corresponding to the pressure waveforms 74a, 74d from FIGS. 3a and 3d that are desired to determine the equilibrium pressure.

Figure 4:
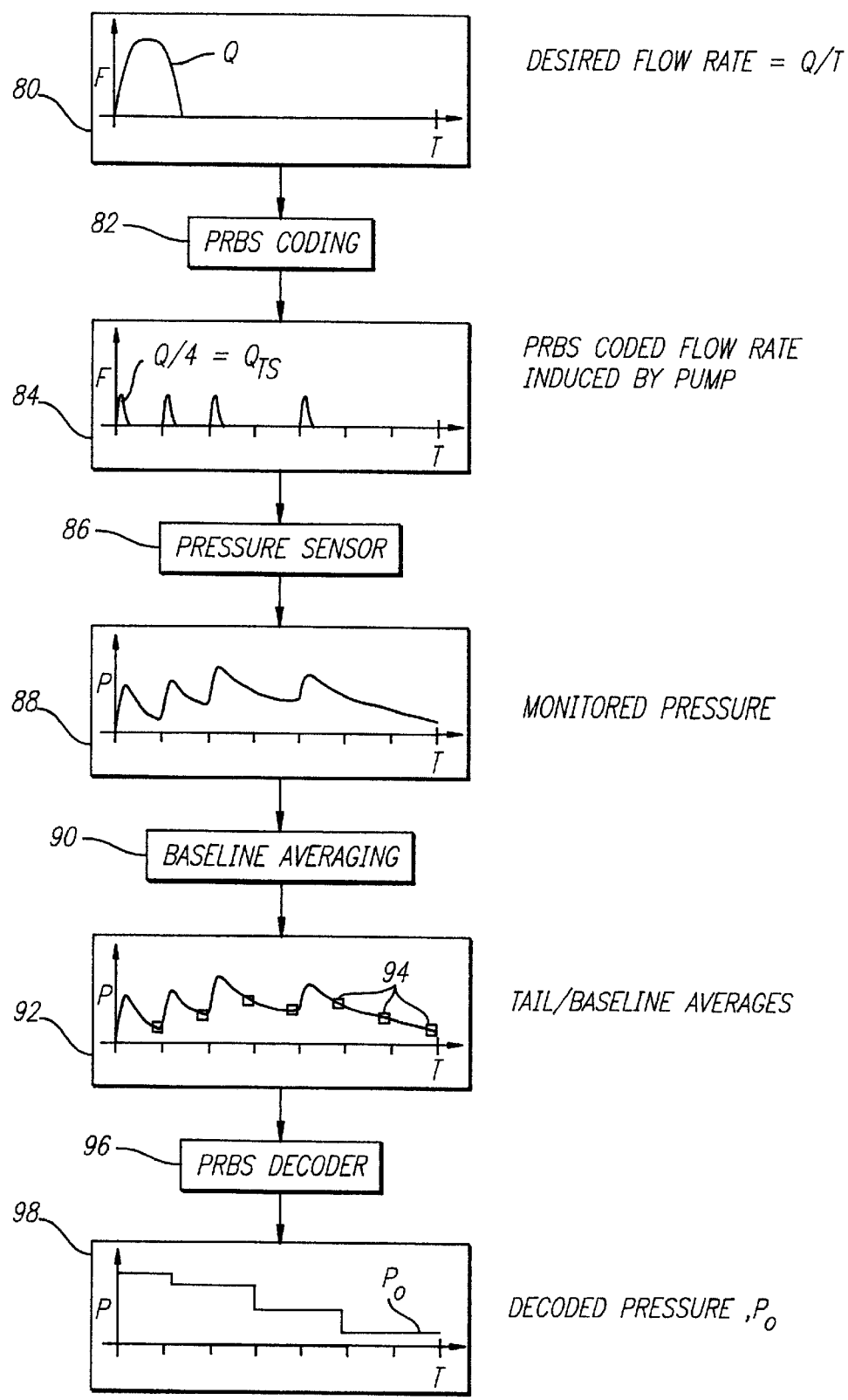
FIG. 4 is a simplified block diagram illustrating the process for generating an estimated pressure waveform using PRBS coding and decoding.

FIG. 4 further illustrates the process of creating a pseudorandom fluid flow, monitoring the resulting pressure, decoding the resulting pressure to create a "virtual" pressure, and determining an estimated equilibrium pressure $P_o$. At 80, a desired flow rate of Q/T, where Q=a selected quantity of fluid and T=the time period, is shown. Rather than deliver the amount Q as a single bolus of fluid in the time period T, a PRBS coder derives a PRBS code 82, which in the embodiment shown is 1 1 1 0 1 0 0. The motor control divides the bolus of fluid into four separate but approximately equal boluses of volume $Q_{TS}$ which are delivered in accordance with the pseudorandom pattern of the PRBS code over the time period, as shown at 84. A transducer or other pressure sensor 86 produces pressure signals to measure the resulting pressure 88.

An averaging process 90, such as block averaging, is used to average a portion of the pressure signals from each timeslot, as depicted at 92. In the embodiment depicted, only the tail portion 94 of each timeslot is averaged. The resulting averaged pressure values are fed into a PRBS decoder 96.

The PRBS decoder 96 processes the averaged pressure values and determines "virtual" pressure values 98. These "virtual" pressure values are used to determine equilibrium pressure ($P_o$), which is then used to calculate the fluid resistance.

Figure 5:
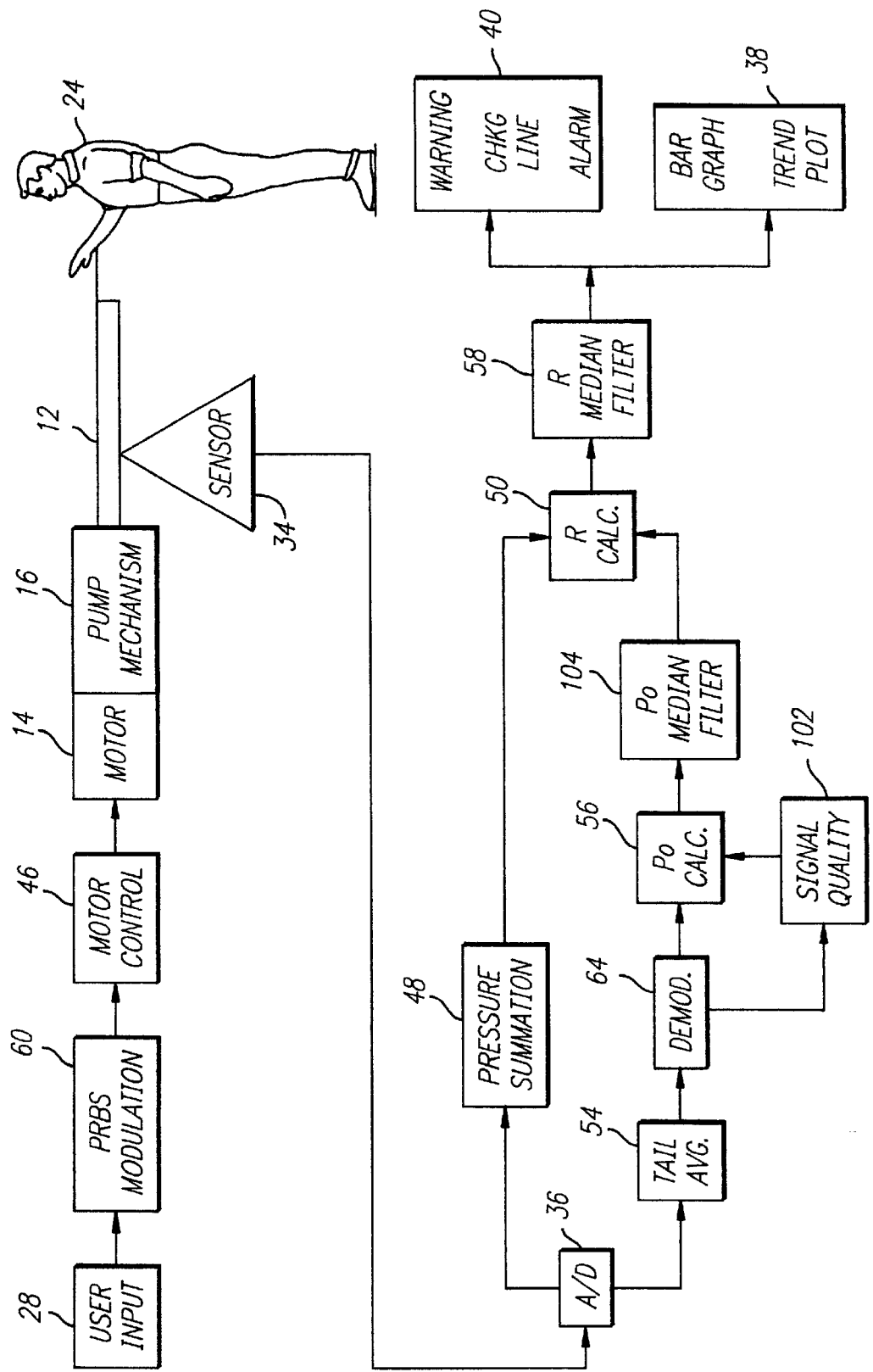
FIG. 5 is a simplified flowchart showing a process for determining resistance according to a preferred embodiment of the invention.

FIG. 5 illustrates in part the process for determining fluid resistance using the pseudorandom flow pattern coder and decoder to determine equilibrium pressure. The user selects a desired flow rate 28 for delivery to the patient 24 through the conduit 12. A PRBS encoder/modulator 60 determines a desired PRBS code and timeslot length based on the user-selected flow rate, and the motor control 46 causes the pump motor 14 and mechanism 16 to induce flow in the conduit 12 in accordance with the PRBS code and timeslot length.

The sensor 34 monitors the resulting pressures in the conduit and provides pressure signals, which pass through the A/D convertor 36 for determination of the fluid resistance. The pressure signals are used to determine a pressure summation 48 over a number of timeslots equal to the PRBS codelength. Portions of the pressure signals are also averaged 54 to determine tail averages or Baseline Sample Averages (BLSAs) for individual timeslots. The BLSAs are then demodulated 64, using an inverse of the PRBS code. The demodulated BLSAs are used for equilibrium pressure $P_o$ determination 56.

In calculating the equilibrium $P_o$ values for various timeslots, the estimated values of $P_o$ can vary in quality and accuracy due to assorted factors, including system noise, large offset changes, and hard occlusions. These factors can create large changes in baseline and/or impedance to occur, thus causing the decoded output to become unstable, which in turn causes the estimated $P_o$ value to have decreased quality and accuracy. To prevent gross miscalculation of resistance due to such conditions, the system determines signal quality 102 by computing a Normalized Sum Absolute Delta's (NSAD) parameter, which provides an estimate of noise. If the NSAD exceeds a set NSAD threshold for a selected timeslot, the estimated $P_o$ calculated for the timeslot is discarded and replaced with the $P_o$ from the most recent timeslot to have a NSAD below the NSAD threshold. Further details of NSAD calculation and use are discussed in greater detail in connection with FIG. 11.

In addition to calculating the NSAD, the accuracy and quality of the estimated $P_o$ values may be further reinforced by filtering each $P_o$ estimate through a $P_o$ median filter 104. Details of the median filter are discussed in greater detail below with respect to FIG. 11.

The estimated $P_o$ value and pressure summations are used for fluid resistance calculation 50 via an equation such as the following:

$$Resistance = \frac{A_p}{A_f} = \frac{\int (P(t) - P_0) dt}{\int F(t) dt}$$

where: $\int f(t)\,dt = Q$ = the known delivered quantity of fluid over the PRBS codelength, and $P_o$ = the estimated equilibrium or offset pressure.

The estimated resistance can be updated for each timeslot, with the calculation using the pressure summation and estimated $P_o$ value from the current timeslot plus the pressure summations of the previous M−1 timeslots, so that data from M timeslots are used to estimate the resistance. This use of data from multiple timeslots increases the accuracy and quality of the updated resistance estimate. The accuracy and quality of the updated resistance can be further improved by using a resistance median filter 58, similar to the median filter 104 described for use with the equilibrium pressure $P_o$. The median filter for the resistance stores the most recent resistance estimates in an array and determines a filtered resistance value. Details of median filter operation are discussed below in greater detail with respect to FIG. 11. In the embodiment shown in FIG. 5, the filtered resistance value is output to the warning/alarm system 40 as well as to a display 38, such as a visual bar graph display and/or a written trend plotter.

Referring now to FIGS. 6 through 13, specific elements of the medium flow rate system and method are described in greater detail, beginning with flow delivery. Typical fluid infusion pumps are driven by stepped motors having a number of steps per pump revolution. Due to the nature of the pumps, the volume delivered by different steps can vary widely. Some pump steps may even deliver negative volumes (i.e., negative flow). To provide consistent delivered fluid volumes, in a preferred embodiment of the invention the pump cycle is divided into a plurality of Supersteps, with each Superstep delivering an approximately equal volume of fluid Qss.

The combination of motor steps into supersteps may be dynamically determined using updated information regarding time-variant or pressure-variant changes in fluid flow per individual steps. However, in a preferred embodiment, division of steps into supersteps is performed using look-up tables specific to a particular pump type.

Figure 6:
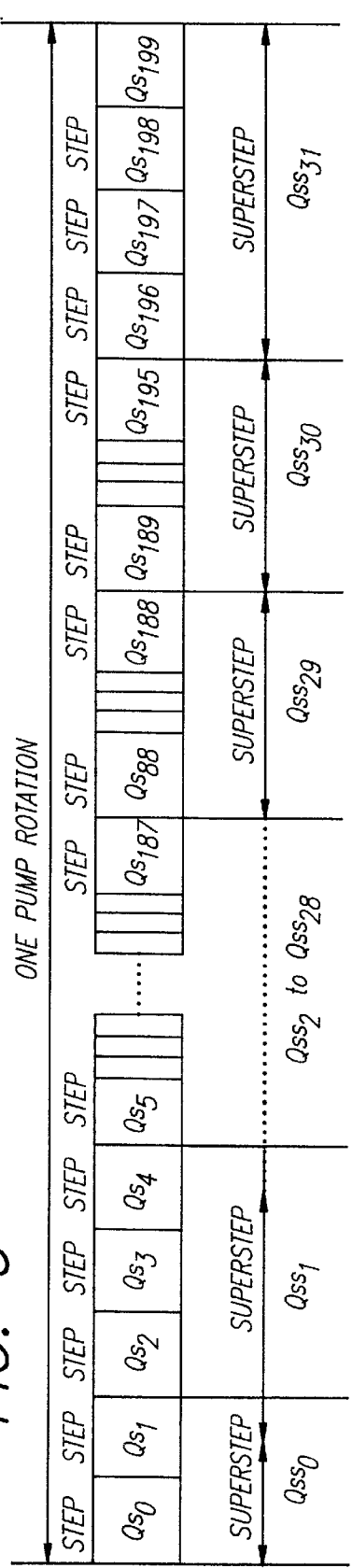
FIG. 6 is a graphical representation depicting sample motor step and Superstep assignments.

In the embodiment shown in FIG. 6, the pump motor provides 200 steps per revolution, with the steps being indexed from 0 to 199. Over one pump revolution, the pump delivers a volume of fluid Qrev, typically expressed in microliters. However, the volume per step (i.e., Qs) varies widely from step to step, with some steps even providing negative volumes. To equalize the flow, the individual motor steps are grouped into a smaller number of movements called Supersteps, with the volume of each Superstep (i.e., Qss) substantially the same as the volume of other Supersteps. In the embodiment shown in FIG. 6, there are 32 Supersteps per pump revolution.

Because the volume pumped per motor step varies widely between steps, the number of steps in individual Supersteps must vary to provide Supersteps with approximately equal fluid volumes. For example, in the grouping shown in FIG. 6 (which is shown only as an example), Superstep 0 (i.e., $Qss_0$, includes just two motor steps ($Qs_0$ and $Qs_1$), Superstep 1 (i.e., $Qss_1$) includes three motor steps ($QS_2$, $Qs_3$ and $Qs_4$), and Superstep 29 (i.e., $Qss_{29}$) includes 101 motor steps ($Qs_{88}$ to $Qs_{188}$). Even though different Supersteps consist of widely varying numbers of motor steps, each Superstep delivers approximately the same fluid volume Qss as other Supersteps.

In a preferred embodiment of the invention, one or more superstep volumes (Qss) are delivered in each timeslot in which fluid is delivered (e.g., each timeslot represented by a binary code of 1). The number of Supersteps of fluid delivered in each fluid-delivery timeslot varies according to the selected flow rate and other system parameters. (No fluid volumes are delivered in non-fluid-delivery timeslots, e.g., timeslots with a PRBS code bit of 0.) Representative numbers of Supersteps per "flow" (i.e., fluid-delivery) timeslot are shown below in Table A.

Timeslot length is determined as a function of the codelength M, the user selected rate, and the number of codes/revolution at the selected rate. Timeslot length is preferably computed to ensure that the specified number of codes are executed per revolution and that the volume produced per code divided by the total time per code produces the user-selected flow rate. In a preferred embodiment, the codelength M, and codes/revolution values are specified by a table lookup as a function of the selected rate, and the timeslot length is either calculated or specified as a function of the selected rate. In a preferred embodiment, timeslots are selected to result in the period T being approximately one minute, thus ensuring that the average flow rate over a period of no more than T will precisely meet the requirements of the operator.

Table A sets forth values of codelength M and codes/revolution in one embodiment of the invention. In the table values set forth in Table A, the values were selected to ensure that the duration of the code is no less than approximately 52 seconds over the flow rate range 0.6 to 49.9 ml/hr for a revolution volume of 183 microliters. Note that the values set forth in Table A are specific to a particular pump apparatus, notably the IVAC Signature Edition, Pump (versions 7100 and 7200), for which the invention divided the 200 pump steps into 32 Supersteps. However, other pump motors and mechanisms are also applicable to the invention, and other values of M, BIC, etc. may be selected for various pumps and other parameters.

TABLE A

| Selected Flow Rate (ml/hr) | Codelength M | Codes Per Revolution | Supersteps Per "Flow" Timeslot |
|---|---|---|---|
| 0.1–0.5 | n/a | n/a | 1 |
| 0.6–1.4 | 7 | 8 | 1 |
| 1.5–3.0 | 15 | 4 | 1 |
| 3.1–6.1 | 15 | 2 | 2 |
| 6.2–12.4 | 15 | 1 | 4 |
| 12.5–24.9 | 15 | 1/2 | 8 |
| 25.0–49.9 | 31 | 1/4 | 8 |

The PRBS codes are preferably of a length that assures that they will evenly fit into a complete pump cycle. To assure an even fit in the pump cycle, the PRBS code should have a number N of flow-delivery timeslots (i.e., timeslots during which a superstep of fluid is delivered, or "active" timeslots), such that the total number of Supersteps per pump cycle (which in the example cited is 32) can be evenly divided by N. In the example shown in Table A, a PRBS code of length 7 will have 4 flow-delivery timeslots, during each of which one Superstep of fluid will be pumped into the conduit by the pump. Since there are 4 active timeslots per PRBS code cycle, it will take 8 PRBS cycles (i.e., 8 PRBS cycles times 4 active timeslots/PRBS cycle) to induce 32 Supersteps.

Similarly, a PRBS code of length 15 has 8 active timeslots, and 32 can be evenly divided by 8. For a PRBS code of length 31, there are 16 active timeslots, which can also be evenly divided into 32.

It should also be noted that, for some of the higher flow rates, more than one Superstep of fluid may be delivered in each active timeslot. In the example set forth in Table A, flow rates over 3.1 ml/hr require two or more Supersteps per timeslot. The number of Supersteps per timeslot is preferably a number that can be evenly divided into the total number of Supersteps per pump cycle.

Where two or more Supersteps of fluid are delivered in a single timeslot, the Supersteps are preferably delivered at the beginning of the timeslot, either as a single bolus of fluid or using the "trilling" method discussed below with respect to FIG. 13.

Figure 7:
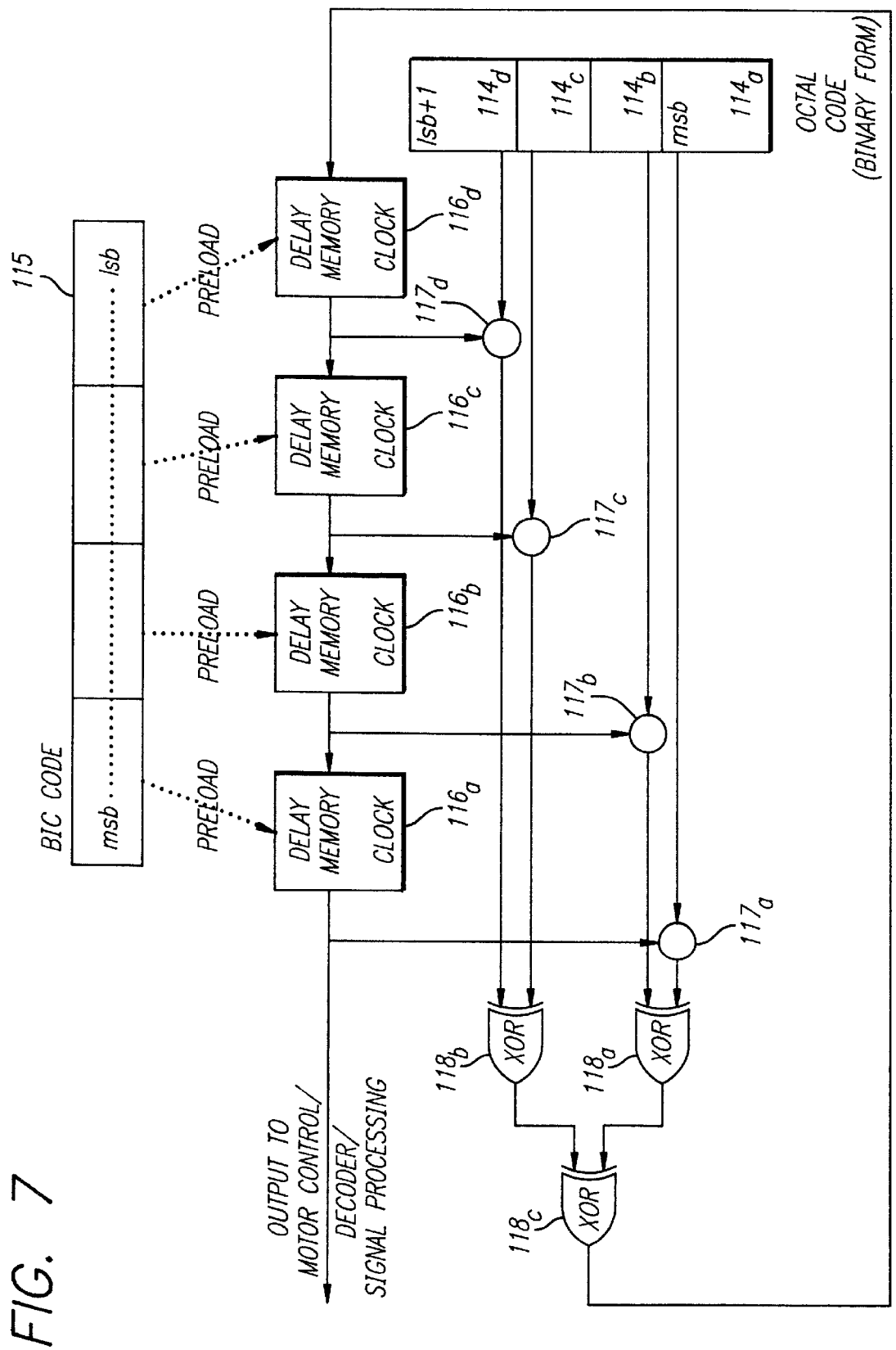
FIG. 7 is a graphical representation of PRBS code generation.

FIG. 7 illustrates a process for generating PRBS codes. Each PseudoRandom Binary Sequence (PRBS) consists of 1 and 0 code values, with each 1 or 0 associated with a Timeslot. Timeslots associated with code values of 1 produce one or more Supersteps of flow at their beginning, while Timeslots associated with code values of 0 produce no flow. The period of code repetition is typically between 40 and 100 seconds, varying with the flow rate. The coded flow pattern produces a cumulative flow equal to that which would have been produced by a nominal constant flow over the time period of the code.

In a preferred embodiment, PRBS codes are produced only in integer lengths of M, where $M=2^k-1$ with k being an integer value. For most applications, codelengths used are $M=7$, 15, or 31. PRBS codes are composed of a series of 1's and 0's, with the number of 1's always being one more than the number of 0's. The count of 1's will always be an even multiple of 2.

In a preferred embodiment, PRBS code sequences are determined using a feedback algorithm such as that shown in FIG. 7. Three key values are used to define the type and phase of any PRBS sequence. The codelength M defines the length of the PRBS code. The OCTAL generator code determines PRBS type, while the Binary Initialization Code (BIC) determines the phase or starting point within the code. Representative codelength M, OCTAL, and BIC values are set forth below in Table B.

TABLE B

| Selected Flow Rate (ml/hr) | Codelength M | OCTAL Code | Binary Initialization Code (BIC) |
|---|---|---|---|
| 0.1–0.5 | n/a | n/a | n/a |
| 0.6–1.4 | 7 | 13 | 111 |
| 1.5–3.0 | 15 | 31 | 1001 |
| 3.1–6.1 | 15 | 23 | 1010 |
| 6.2–12.4 | 15 | 23 | 1101 |
| 12.5–24.9 | 15 | 23 | 1100 |
| 25.0–49.9 | 31 | 75 | 11101 |

The OCTAL values in Table B are from Zeimer and Peterson, *Digital Communications And Spread Spectrum Systems*, page 390, MacMillan Publishing Co., New York. The OCTAL code, which is expressed in the table in a base 8 (i.e., octal) format, determines which of several possible PRBS codes of a given length will be formed.

Certain codes and relative rotations (i.e., starting points) have been determined to provide optimal performance for particular pumps to minimize effects of mechanism and sensor generated artifacts. The BIC values in Table B, which determine the phase or starting point within the code, were empirically determined based on flow characteristics of a particular pump, as discussed in greater detail below with respect to FIG. 12.

In the PRBS coding process shown in FIG. 7, the selected OCTAL code is converted into a binary format to create an array of 1 and 0 multipliers. The least significant bit (lsb) of the OCTAL code is discarded, and the remaining code is arranged, from the next-to-least significant bit (lsb+1) (the least significant bit having been discarded), to the most significant bit (msb) in an the Octal Code (binary form) array 114. The Octal Code (binary form) array is used to operate on the outputs of "degree" number of shift registers.

The Binary Initialization Code (BIC) is used to establish the initial value of the shift registers and thus determine the first few bits of the PRBS code and the relationship of the PRBS code to the physical rotation of the pump mechanism. The BIC phase value corresponds to the motor/rotation monitor being aligned to start Superstep 0. As shown in FIG. 7, the BIC is arranged, from least significant bit (lsb) to most significant bit (msb), in an array 115. Upon system activation, the BIC array is used to preload the generator array elements 116.

In a first operation, the Octal Code (binary form) array elements (114$_a$ to 114$_d$) are multiplied with generator array elements (116$_a$ to 116$_d$), as shown by multipliers (117$_a$ to 117$_d$). The resulting values are processed through a series of EXCLUSIVE/OR ("XOR") function gates 118, with each XOR function gate receiving a pair of values as an input and outputting either a 1 or a 0. The XOR gates output a 0 in response to an input of a (1 and 1) or a (0 and 0), and output a 1 in response to an input of a (1 and 0) or a (0 and 1). As shown in FIG. 7, the two values produced by two of the multipliers (117$_a$ and 117$_b$) are inputted to one XOR gate (118$_a$), and the two values produced by the remaining two multipliers (117$_c$ and 117$_d$) are initially passed to another XOR gate (118$_b$). Each of these XOR gates (i.e., 118$_a$ and 118$_b$) output a single 1 or 0 value. The outputs of these XOR gates (118$_a$ and 118$_b$) are inputted to a third XOR gate 118$_c$, which outputs a single 1 or 0 value.

The left-most value of the generator array (i.e., the value in register 116$_a$) is outputted to motor control as the first element in the PRBS array. The values in all the other registers shift one position to the left, leaving the last register 116$_a$ empty. The output value from the third XOR gate 118$_c$ is then entered into the last register 116$_a$.

The process depicted in FIG. 7 is specific to a 4-element BIC. However, similar processes can be used to generate PRBSs using BICs of different lengths.

The above-cited process is repeated until M elements of the PRBS code have been generated.

The above discussion concentrates on the use of PRBS codes. However, pseudorandom codes other than Pseudo-Random Binary Codes are also applicable to the current invention. For example, a PseudoRandom code consisting of non-binary values, such as a 4-bit code having values of 2, 4, 0, and 3, could be used. Even non-integer values could be used, such as a 3-bit code having values of 0.6, 1.2, 0.8. In such an embodiment, three boluses of fluid would be delivered, each having volumes of proportional to the particular bit (i.e., 0.6, 1.2, 0.8). Alternatively, the boluses might be of approximately the same size, but the spacing between boluses may be varied in proportion (either direct or inverse) with the particular bit value.

A pseudorandom code is one for which its frequency response contains energy at all frequencies. This allows for a suitable inverse code to be created. Non-binary and non-integer values are applicable to the current invention, in that they can be used to accurately estimate equilibrium pressure and determine "virtual" waveforms. However, the use of non-binary and non-integer values complicates the processing involved. Restricting the codes to PseudoRandom Binary Codes, such as 1101, simplifies processing and improves system efficiency. Accordingly, PRBS codes are the preferred embodiment of the current invention.

As was shown in FIGS. 3 and 4, flow delivered in accordance with a PRBS code results in a corresponding pressure waveform, which can be monitored with a transducer or other sensor to produces corresponding pressure signals. The pressure signals can be decoded via a PRBS decoder to create a corresponding "virtual" waveform. However, because pressure sensors typically provide numerous pressure signals per second, hundreds of pressure signals are created for most timeslots. Decoding all the pressure signals for each timeslot is extremely processor-intensive. However, by averaging select pressure signals from each timeslot, and only decoding a single average value from each timeslot, the amount of decoding required can be drastically reduced while still maintaining accuracy of the $P_o$. Rather than decoding each and every pressure signal in a timeslot, an average can be taken of just a portion of the timeslot, and this average value can be decoded to determine an estimated $P_o$. The estimated $P_o$ determined using pressure signal averaging is remarkably close to the estimate $P_o$ determined by decoding each and every pressure signal. However, the processing requirements are drastically reduced using pressure signal averaging.

Figure 8:
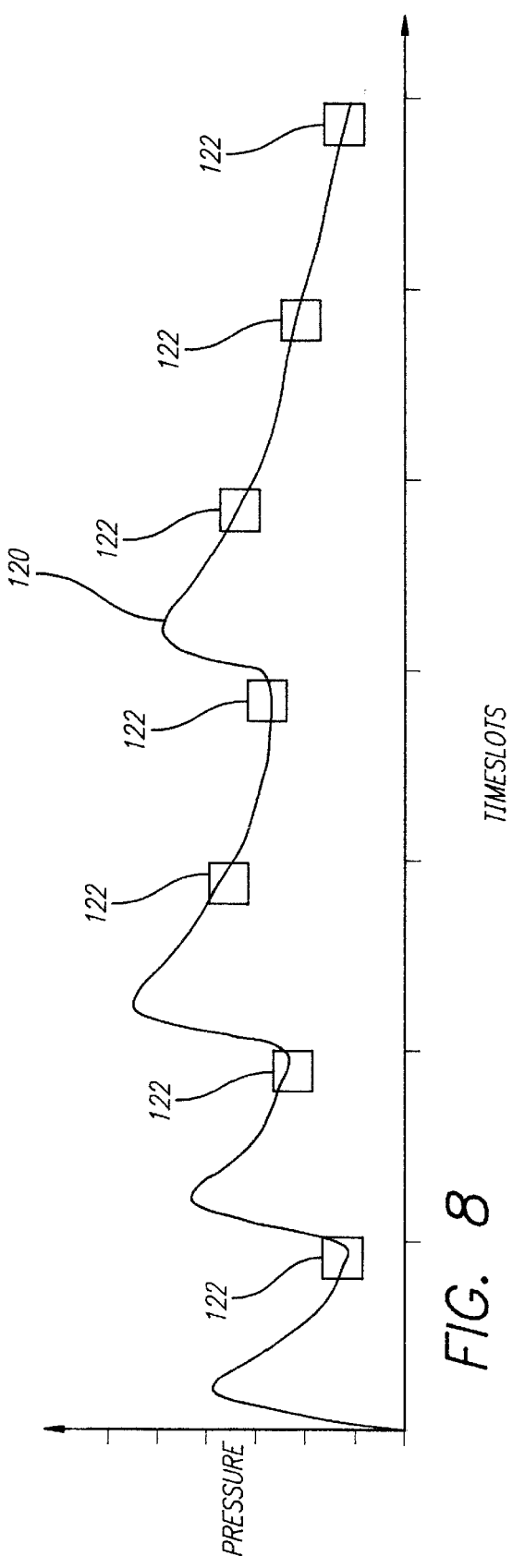
FIG. 8 is a graphical representation of pressure responses showing baseline sample averaging regions.

FIG. 8 shows a pressure waveform 120 in a preferred embodiment of pressure signal averaging, wherein the averaged portion 122 of the timeslot comprises the final 25% of the "tail" portion. This average is known as the Baseline Sample. This process minimizes the effects of high frequency artifacts, improves effective resolution, and reduces decoder operations.

It should be noted that the pressure signal averaging need not be confined only to 25%, or to just the tail portion of the timeslot. Other portions and other percentages of the pressure signal could also be averaged and still give relatively accurate $P_o$ estimates. An accurate $P_o$ estimate can even be made using the average of pressure signals over the entire timeslot. When the average is then decoded, the resulting estimated $P_o$ is remarkably close to the estimated $P_o$ determined by averaging only the tail portion of the timeslot or by directly decoding each and every pressure signal over the entire timeslot.

For decoding, each averaged value is entered into a shift register array of length equal to that of the PRBS code (i.e., length=M). The shift register array comprises an averaged pressure value from the most recent M timeslots. The averaged pressure values are then decoded, and the decoded pressure values used to determine an estimated $P_o$.

As an additional enhancement to accuracy of the resistance determination, the digital pressure signals received from the A/D converter may be premultiplied prior to the averaging process. Many A/D convertors have a resolution of about only about 0.5 mm Hg per count, which is insufficient for accurate measurement of low resistances at low rates. In a preferred embodiment, additional resolution is obtained by premultiplying raw A/D count values by 256 prior to the averaging process. The premultiplied values are then averaged, and the averaged result, now in scaled units, is input to the PRBS decoder to produce scaled-up response values.

FIG. 9 illustrates a process for decoding pressure signals using a PRBS decoder. Decoding the resulting pressure signals requires $M^2$ addition or subtraction operations per resistance calculation, and M array rotate operations per resistance calculation. On the first ad sample of each timeslot, motor control passes to the decoder the current encoding value (0,1). The decoder will enter into an M element shift array the value −1 if the encoding value is 0, or a +1 if the encoding value is 1. The resulting array of +1's and −1's, known as the Cbit array, will be used for decoding. The Cbit array is initialized to all 0's whenever RUN is activated. Since $P_o$ estimate selection logic will preclude use of the decoded outputs until M timeslots elapse following RUN activation, the Cbit array will be filled with correct values by the time it needs to be used.

The decoded output for an M length array of pressure samples P may be expressed mathematically as:

$$DecoderOut(i) = \sum_{k=0}^{M-1} Cbit(_{(i+k)_{modulo\,M}}) P(k)$$

where the index i runs from 0 to M−1, and the 0th index refers to the earliest decoder value. Since the Cbit array contains only 1 and −1 values, the multiplication above may be replaced by a logical test and an add or subtract operation, depending on the value of the Cbit array element.

FIG. 9 illustrates the decoding process for a simple M=3 code used to decode a 3-bit array of pressure baseline sample averages (BLSAs). Each sample box contains the index of the value to be used in processing, with 0 representing the current sample (or unrotated code bit). The Cbit array values are +1, +1, and −1, corresponding to a PRBS code of 1 1 0.

Figure 9A:
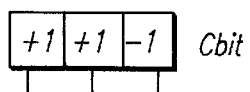
FIGS. 9(A), 9(B) and 9(C) are graphical representations of PRBS decoding.
Figure 9A:
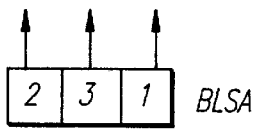
Figure 9A:
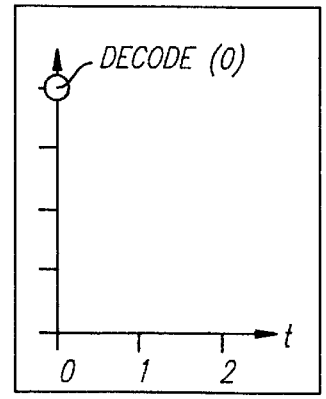

FIG. 9a shows the alignment of the Cbit array and the BLSA array elements within shift registers Cbit and BLSA. Each time a timeslot is completed, the Encoder replaces the rightmost (current−indexed 0) element of Cbit with its current value (1 or −1). Previously held values within Cbit are shifted to the left, and the oldest (leftmost) is discarded. Similarly, with the completion of each timeslot, the Baseline Sample Averager produces a BLSA value which is placed in the rightmost (current−indexed 0) element of BLSA. Previously held values within the BLSA array are shifted to the left, and the oldest (i.e., leftmost) value is discarded.

Following the loading and shifting of the arrays, the actual decoding of the BLSA array occurs. As shown in FIG. 9a, the product of each corresponding element of the two shift register arrays is formed. Then the sum of these products is taken. This result will produce the earliest "virtual pressure impulse" response, which is indexed as element 0 in the time line graph to the right of the registers and denoted Decode (0).

Figure 9B:
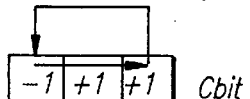
Figure 9B:
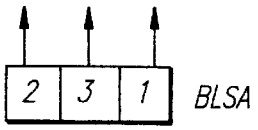
Figure 9B:
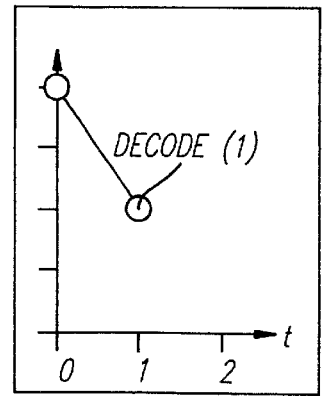
Figure 9C:
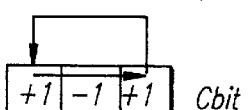
Figure 9C:
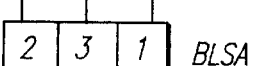
Figure 9C:
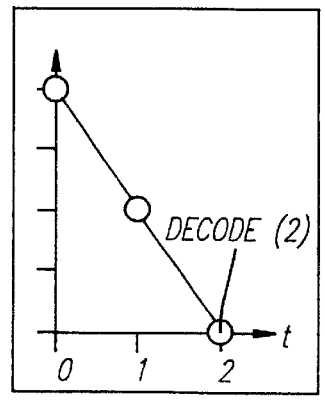

Referring now to FIG. 9b, the elements of Cbit are rotated, so that the newest element is moved into the position previously occupied by the eldest, and all other elements (including the eldest element) are shifted one register to the right. All these operations are preferably performed with the assistance of a temporary holding register (not shown) or equivalent functionality of a microprocessor so that no data elements are lost.

Again, the corresponding products for each shift register position are formed, and the sum of the products computed. This produces the next-to-earliest "virtual pressure impulse" response element, which is indexed as element 1 in the time line graph to the right of the registers and denoted Decode (1).

The process of rotation of the elements, multiplication of corresponding elements, and summing the products is repeated for the remaining Cbit elements, which in the 3-element array of FIG. 9 is only one additional element. As shown in FIG. 9c, the resulting element is indexed as element 2 in the time line graph to the right of the registers and denoted Decode(2).

The above-cited decoding process is known generically as "circular convolution" and is well known in the signal processing art.

Another example of PRBS decoding is shown in Table C. In the example shown, a PRBS code of 1 1 1 0 1 0 0, which was used to generate a flow in a conduit, is used to decode an array of measured pressure signals, which in the example shown is (4 5 6 4 5 4 3). For the first row, i.e., row A, the binary values (1 1 1 0 1 0 0) are replaced with a plus (+) or minus (−) sign, with a plus (+) sign replacing 1 values, and a (−) sign replacing 0 values, resulting in the series (+++−+−−). For each subsequent row (i.e., rows B through G), the resulting series of +/− signs are each shifted one place to the right (with the +/− sign in the rightmost column transferring to the leftmost column).

TABLE C

|   | 4 | 5 | 6 | 4 | 5 | 4 | 3 |   |
|---|---|---|---|---|---|---|---|---|
| A | + | + | + | − | + | − | − | 9 |
| B | − | + | + | + | − | + | − | 7 |
| C | − | − | + | + | + | − | + | 5 |
| D | + | − | − | + | + | + | − | 3 |
| E | − | + | − | − | + | + | + | 3 |
| F | + | − | + | − | − | + | + | 3 |
| G | + | + | − | + | − | − | + | 1 |

The resulting +/− signs in rows A through G are then applied to the pressure values to be decoded, and the resulting values are added together across each row (A through G). Thus, row A, when applied to an array of seven pressure averages pressure values (4, 5, 6, 4, 5, 4, 3), translates to (+4, +5, +6, −4, +5, −4, −3), which when added together results in a value of +9. Row B translates to (−4, +5, +6, +4, −5, +4, −3), which when added together results in a value of +7. Row C translates to (−4, −5, +6, +4, +5, −4, +3), which when added together results in a value of +5. Rows D through G result in values of 3, 3, 3, and 1, respectively. Accordingly, the decoded array, which represents the decoded pressure waveform, is (9 7 5 3 3 3 1). (Note that the average pressure values actually shown in Table C are not based upon actual measurements, but are sample numbers that are used merely for illustrative purposes.)

After the pressure signals have been decoded, they can be used to determine an estimated $P_o$. Various methods can be used to estimate $P_o$, with the preferred method varying depending on the user-selected flow rate, the time since start up, the values of the decoded pressure responses, and previous resistance estimates. In a preferred embodiment of the invention, the method for determining estimated $P_o$ is selected as a function of various parameters, as set forth in Table D.

Various methods for determining the estimated $P_o$ are discussed below. The logic for selecting a particular method for determining $P_o$ is shown in Table D.

For user selected flow ranges of 0.5 ml/hr or less, there is typically sufficient time in each timeslot for the monitored pressure to decay to $P_o$. However, transient pressure and sensor anomalies can cause brief spikes or other inconsistencies in the monitored pressure. To reduce the impact of such monitored pressure inconsistencies, the estimated $P_o$ is determined as the average of the final portion, such as the final 25%, of the pressure readings in the timeslot. No pseudorandom coding or decoding is involved. Determining $P_o$ for low flow rates, such as flow rates of 0.5 ml/hr or less, is discussed in greater detail below with respect to FIGS. 14 and 15.

Another group of techniques for determining $P_o$ that is useful when pseudorandom coding and decoding are used is referred to as Three Point Block Averaging. Three point block averaging is a process whereby the pressure samples that are output from the decoder, which has M number of samples (i.e., a length of M), is divided into three blocks of samples, and the average of each block of samples is taken. The resulting block averages are then used to determine an estimated $P_o$.

Of course, M is not always evenly divisible by three. However, where M is not evenly divisible by three, M−1 will always be divisible by three. Accordingly, where M cannot be evenly divided by three, the last sample of the decoded output is discarded, which gives a remaining number of samples that is evenly divisible into three blocks.

Figure 10:
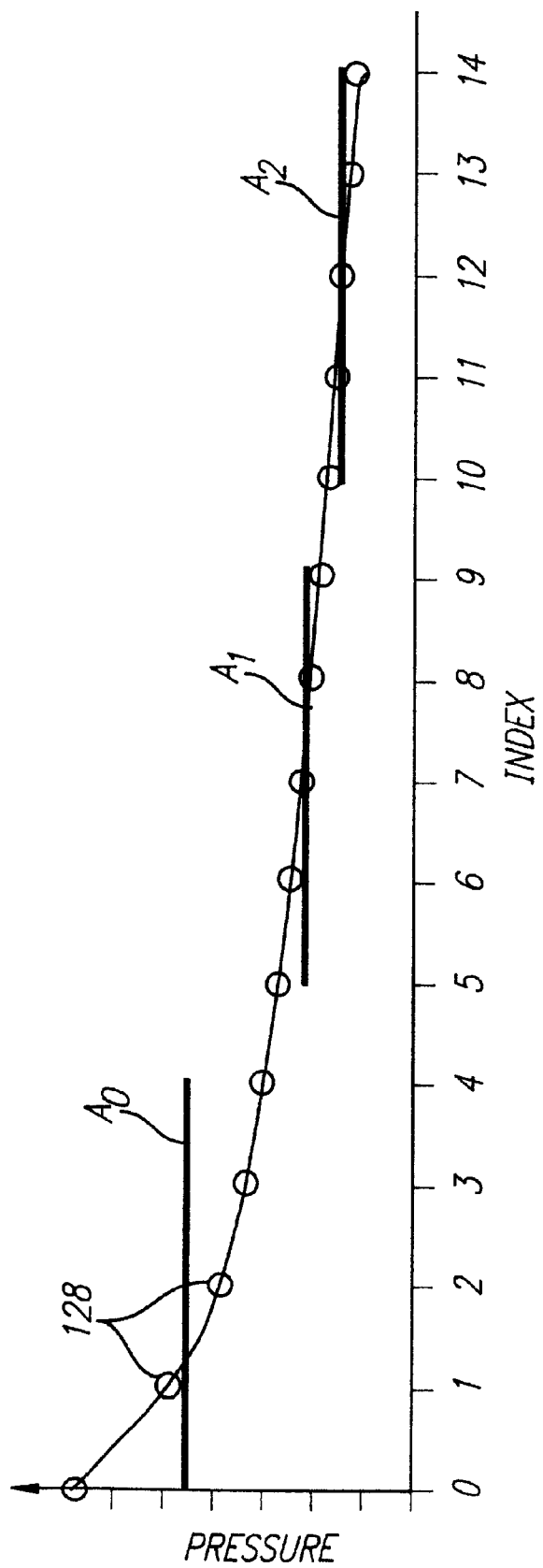
FIG. 10 is a graphical representation of decoded pressure responses showing block averages.

As shown in FIG. 10, the average of each block of an output of decoded samples 128 is shown, where M=15. The resulting averages are defined as follows:

portion of the pressure signals from each timeslot. These tail averages are not decoded. Instead, the tail averages are themselves averaged, resulting in a single average value. The average value is then used as the estimated $P_o$. This method is generally effective under conditions where low resistances are expected, such as where the most recent

TABLE D

| Elapsed Timeslots Since Stopped ≤ M? | NSAD > NSADthresh? | NSAD < NSADminthresh or A2 > A1? | Filtered Resistance < Resistance Threshold | SELECTED FLOW RATE (in ml/hr) | | | | | | |
|---|---|---|---|---|---|---|---|---|---|---|
| | | | | 0.1–0.5 | 0.6–1.4 | 1.5–3.0 | 3.1–6.1 | 6.2–12.4 | 12.5–24.9 | 25.0–49.9 |
| TRUE | ANY | ANY | ANY | Timeslot Tale Average | Held Po Value | Held Po Value | Held Po Value | Held Po Value | Held Po Value | Held Po Value |
| FALSE | TRUE | ANY | ANY | Timeslot Tale Average | Last Po | Last Po | Last Po | Last Po | Last Po | Last Po |
| FALSE | FALSE | TRUE | TRUE | Timeslot Tale Average | Average of Most Recent M Baseline Averages | Average of Most Recent M Baseline Averages | Average Of A1 and A2 | Average Of A1 and A2 | Average Of A1 and A2 | Average Of A1 and A2 |
| FALSE | FALSE | TRUE | FALSE | Timeslot Tale Average | Average Of A1 and A2 | Average Of A1 and A2 | Average Of A1 and A2 | Average Of A1 and A2 | Average Of A1 and A2 | Average Of A1 and A2 |
| FALSE | FALSE | FALSE | TRUE | Timeslot Tale Average | Average of Most Recent M Baseline Averages | Average of Most Recent M Baseline Averages | A2 | A2 | A2 | $A2 + \frac{D2^2}{(D2-D1)}$ |
| FALSE | FALSE | FALSE | FALSE | Timeslot Tale Average | A2 | A2 | A2 | A2 | A2 | $A2 + \frac{D2^2}{(D2-D1)}$ |

A0 = the average of the first block of samples;
A1 = the average of the second block of samples;
A2 = the average of the third block of samples.

Intermediate values (i.e., the differences between adjacent average values) are as follows:

$$D_1 = A_0 - A_1$$

$$D_2 = A_1 - A_2$$

Using all or portions of the above values, i.e., $A_0, A_1, A_2, D_1$, and $D_2 P_o$ can be estimated. Various techniques for using $A_0, A_1, A_2, D_1$, and $D_2$ to determine the estimated $P_o$ are set forth below. Which technique to use depends on the particular parameters, such as pump characteristics, flow rate, NSAD status, etc. In a preferred embodiment of the invention, the technique for determining $P_o$ is selected using the parameters set forth in Table D.

Formulas for determining the estimated $P_o$ that use three point block averaging include the following:

$$P_o = A_2 + \frac{(D_2)^2}{D_2 - D_1}$$

$$P_o = A_2$$

$P_o$ = Average of $A_1$ and $A_2$

Another method for determining $P_o$, but without using three point block averaging, involves averaging just the tail previous measurement from the output of the resistance median filter indicated a low resistance value.

As shown by the above, there are a variety of methods to estimate $P_o$. The suitability of particular methods depends on various conditions, such as flow rate, set compliance, etc. Determining the optimum method can require extensive testing of the particular equipment. Table D shows various preferred methods for estimating $P_o$, with the preferred method a function of selected flow rate, NSAD factor (i.e., stability of the decoded signal), calculated resistance, and time the system has been in operation.

When large changes in baseline or impedance occur (due to such factors as noise, large offset changes, or hard occlusions), the decoded output can become unstable. To prevent gross miscalculations of resistance under such conditions, an alternate estimation method must be selected. A preferred embodiment of a $P_o$ estimation selection logic, such as the one shown in Table D, requires a method to determine stability of the decoded signal. This is achieved by computing an "estimate noise" parameter known as Normalized Sum Absolute Delta's (NSAD). NSAD is defined as the sum of the absolute value of the differences $D_1$ and $D_2$ divided by the product of codelength (M) and the number of Supersteps per timeslot (to normalize for different codes and drive patterns). NSAD is thus defined by the following formula:

$$NSAD = \frac{(|D_1| + |D_2|) \text{ mm Hg}}{CodeLength(M) * SuperstepsPerTime}$$

NSAD is compared to a threshold $NSAD_{thresh}$, which is itself dependent on the selected flow rate. Preferred embodiments of values of $NSAD_{thresh}$ for various selected flow rates are shown in Table E. If NSAD exceeds $NSAD_{thresh}$, a "true" condition is input into the $P_o$ determination method selection logic process, as shown in Table D.

TABLE E

| Selected Flow Rate (ml/hr) | $NSAD_{thresh}$ |
|---|---|
| 0.1–0.5 | n/a |
| 0.6–1.4 | 4 |
| 1.5–3.0 | 4 |
| 3.1–6.1 | 7 |
| 6.2–12.4 | 7 |
| 12.5–24.9 | 7 |
| 25.0–49.9 | 7 |

When fluid resistances are very low, the difference values $D_1$ and $D_2$ become very small. Where $P_o$ is determined using the formula with the value $(D_2-D_1)$ in the denominator This can cause the difference $D_2-D_1$ to approach zero. Where that difference (i.e., $D_2-D_1$) is used in the denominator of an equation for determining $P_o$, such as Equation 8 above, a large and unstable $P_o$ estimate can result. To identify situations that might yield such unstable results, the NSAD value is compared with a minimum NSAD threshold value $NSAD_{minthresh}$, which in a preferred embodiment is equal to 0.25 mm Hg/(M * SuperstepPerTimeslot), and the logical result is used in the $P_o$ estimation method selection processor outlined in Table D.

When the resistance becomes relatively low, the most stable method for estimating $P_o$ uses a direct average of the M available Baseline Sample Average (BLSA) values as the estimated $P_o$, without any decoding of the pressure averages. This technique is used when output from the Resistance Estimation Filter is less than a resistance threshold $R_{thresh}$, which in a preferred embodiment is 600 fluid ohms.

Following a period of no flow, such as just after system start up, the output from the PRBS decoder will be incomplete and inaccurate until at least M timeslots have elapsed since the mechanism was started. Accordingly, there is insufficient data in the system to accurately calculate an estimated $P_o$. Where less than M timeslots have elapsed since the mechanism was started, other methods for selecting $P_o$ estimation value must be used. Two such methods are set forth in Table D. In one embodiment, for selected flow rates between 0.6 to 50 ml/hr, the $P_o$ value used is the pressure that was measured in the conduit just prior to the beginning of pump operation (i.e., just before system run). For rates of 0.5 ml/hr or less, the Baseline Sample Average for the individual timeslot alone is used, in combination with the special "low flow rate" mode of resistance calculation discussed in greater detail below with respect to FIGS. 14 and 15.

Spurious signals and other transient anomalies can occasionally result in an inaccurate estimated $P_o$ for occasional timeslots. As shown in FIG. 11, the impact of such inaccurate $P_o$ estimates can be reduced and sometimes eliminated by using a median filter. The median filter includes an array for storing the most recent $P_o$ values. In a preferred embodiment shown in Table F, the $P_o$ filter array has a size M, so that it stores the $P_o$ values for one codelength.

TABLE F

| Selected Flow Rate (ml/hr) | $P_a$ Filter Array Length |
|---|---|
| 0.1–0.5 | n/a |
| 0.6–1.4 | M (7) |
| 1.5–3.0 | M (15) |
| 3.1–6.1 | M (15) |
| 6.2–12.4 | M (15) |
| 12.5–24.9 | M (15) |
| 25.0–49.9 | M (31) |

Figure 11:
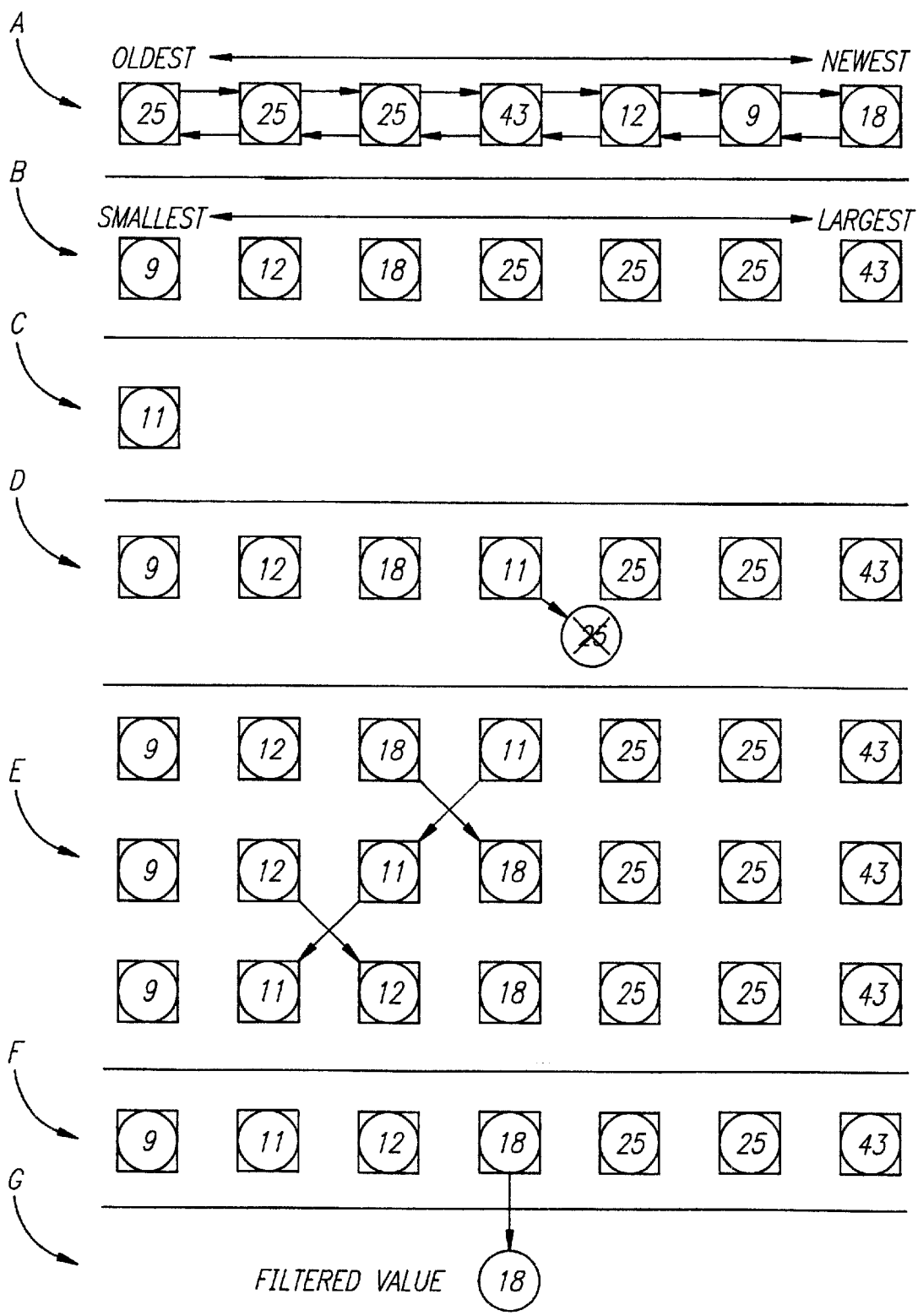
FIG. 11 is a simplified block diagram showing median filtering.

The median filter process shown in FIG. 11 involves an array of length 7. The array stores the most recent 7 values. The relative age of individual data elements is maintained in a linked list, shown at (A), that shows the relative ages from oldest to newest.

The data elements are maintained and sorted in an array, shown at (B), from smallest to largest. When a new value is presented, such as the value "11" shown at (C), the oldest value is discarded, which in the example shown at (D) is the value "25". The new value takes the place of the discarded old value. Note that in the example shown, the array was preloaded before operation with the value "25" in each array slot. Prior to introduction of the most recent value (i.e., "11"), only four new values ("9", "12", "18", and "43") were added to the array.

The array with the newly added value ("11") is sorted, such as through a typical bubble sorting method, to place all values in order from smallest to largest, as shown at (E). The resulting ordered array, shown at (F), has all elements from smallest to largest. The center value, which in the example shown is "18", is the new median filtered value, as shown at (G).

Note that filtering could also be performed by other methods, such as simple averaging of the current $P_o$ value with other recent $P_o$ values. However, median filtering has certain advantages over averaging, particularly in eliminating the effects of extreme values, such as the "43" that appeared in the example shown in FIG. 11.

Another method for improving the accuracy of the $P_o$ and resistance calculations involves the use of the BIC code, which is used to reduce the impact of revolution synchronous noise sources. Revolution synchronous noise sources are anomalies in pressure signals that occur predictably within specific Supersteps. These noise sources can corrupt the decoded waveform, causing large inaccuracies in estimated $P_o$. Revolution synchronous noise sources include mechanism-induced sensor offset shifts and variations in flow between Supersteps.

Figure 12A:
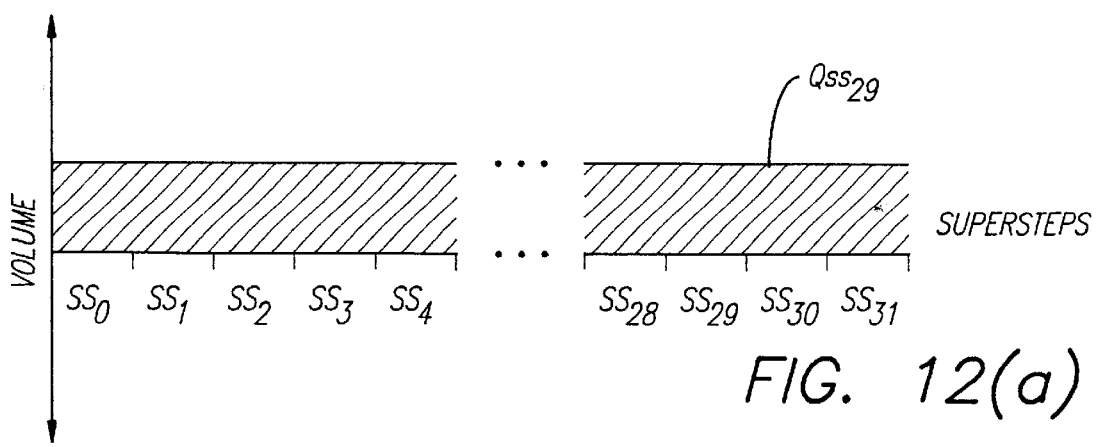
FIGS. 12(a) and 12(b) are graphical representations of flow waveforms resulting from adjacent pump steps.

Variations in flow volume Qss between Supersteps can range from small variations to situations where a Superstep actually produces negative flow. Although the Supersteps are selected to deliver approximately equal volumes of fluid, as shown in FIG. 12a, fluid delivery varies between Supersteps over time, depending on various system parameters such as downstream pressure. In a preferred embodiment, the Supersteps are predetermined based upon pump characteristics, and are not dynamically adjusted to compensate for time-variant changes in fluid delivery volumes. However, under some circumstances, such as where the downstream pressure is large, the volumes delivered by different Supersteps can vary widely, even to the point where one or more Supersteps may deliver negative volumes of fluid. For example, while a pump operating with relatively low downstream pressures may produce the substantially equal fluid delivery volumes shown in FIG. 12a, that same pump operating with higher downstream pressures may deliver varying fluid delivery volumes such as those shown in FIG. 12b.

Figure 12B:
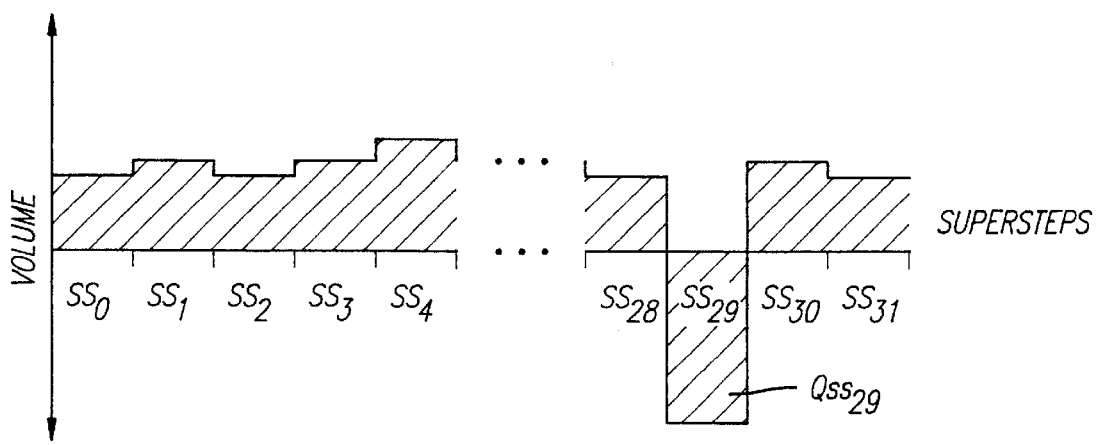

Although most Supersteps either experience no change or only a very small change in delivered volumes due to downstream pressure, one or more Supersteps can see variations in their delivered volume. For example, in the hypothetical 200-step, 32-Superstep pump cited by way of example in FIGS. 12a and 12b, Superstep 29 ($SS_{29}$) can go from a small positive delivered volume $Qss_{29}$ at low downstream pressures (FIG. 12a) to a large negative delivered volume $Qss_{29}$ at higher downstream pressures (FIG. 12b). Such time and pressure-variant changes, i.e., "artifacts," in Superstep delivered volumes can cause problems with accurately determining equilibrium pressure $P_o$ and resistance R.

Noise synchronous sources are generally predictable in nature. The problems caused by revolution synchronous noise sources with determining $P_o$ and R can largely be eliminated by pairing a "noisy" Superstep (such as the negative-volume Superstep $SS_{29}$ from FIG. 12b) with a particular PRBS codestep. This is accomplished by the Binary Initialization Code ("BIC"), which is used to establish the initial value of the shift registers and thus determine the relationship of the code to the physical rotation of the pump mechanism. The BIC phase value typically corresponds to the motor/rotation monitor being aligned to start Superstep 0 ($SS_0$). Correct phasing of the code relative to the mechanism helps to minimize artifact-induced errors in the $P_o$ estimate. In a preferred embodiment, the BIC is empirically determined for particular pumps and flow rates, depending on the noise synchronous sources for the particular system. For the 200-step IVAC Signature Edition Pump (versions 7100 and 7200), preferred BICs for various flow rates were shown previously in Table B.

Figure 13A:
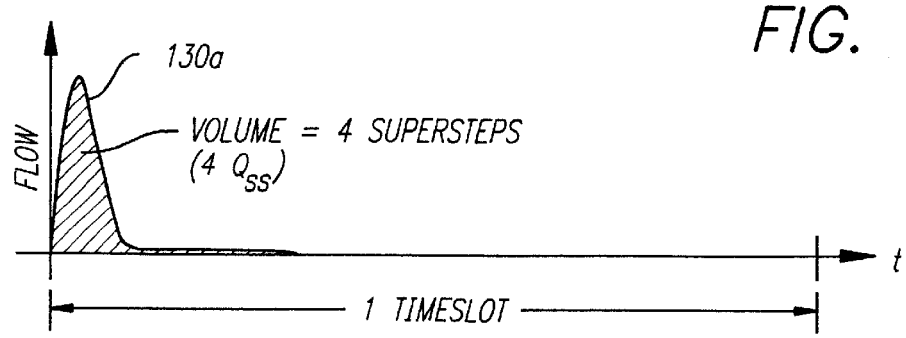
FIG. 13a is a graphical representation of flow waveforms according to an acceleration/deceleration waveform.

In order to maximize the time allowed for the pressure to decay while still maintaining timeslots of a reasonably small size, it is generally desirable to deliver fluid in a narrow time range, such as the very beginning, of a timeslot. Such delivery preferably occurs by delivering one or more Superstep volumes (Qss) using a single acceleration/deceleration current waveform. For example, FIG. 13a shows four Supersteps delivered as a single acceleration/deceleration waveform 130. The use of acceleration/deceleration current waveforms is described in detail in pending U.S. patent application Ser. No. 08/526,468, which is incorporated herein by reference.

However, where more than one Superstep occurs in a single timeslot, or where a single Superstep involves the delivery of a substantial amount of fluid, delivering such a large amount of fluid in a single acceleration/deceleration waveform 130a, as shown in FIG. 13a, may create undesirably high instantaneous flow rates, which can create "sympathetic flow" from the primary fluid source during secondary delivery. Additionally, using a single acceleration/deceleration waveform can create undesirably high instantaneous pump speeds.

Figure 13B:
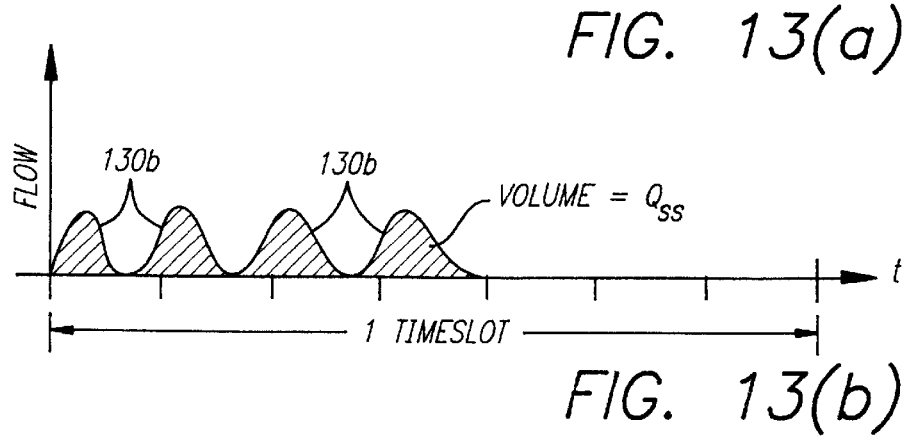
FIG. 13b is a graphical representation of flow waveforms according to trilled acceleration/deceleration waveforms.

To reduce instantaneous pump and fluid injection speeds, the fluid delivery may be "trilled." Trilling involves breaking the single waveform into a plurality of smaller waveforms 130b, as shown in FIG. 13b, with each small waveform preferably following an acceleration/deceleration waveform. In the embodiment shown in FIG. 13b, four Superstep volumes (4 Qss), which were delivered as a single bolus waveform 130a in FIG. 13a, are delivered as four separate waveforms 130b, with each small waveform 130b delivering one Superstep volume (Qss) of fluid. The individual waveforms 130b are preferably spaced immediately adjacent to each other so that fluid delivery occurs in a narrow time period, with the remainder of the timeslot allowing for the pressure to settle/decay to allow for more accurate estimation of $P_o$.

In addition to an accurate $P_o$ value, determining resistance also requires determination of the sum of the pressure signals (i.e., pressure samples) for each timeslot. Summing the pressure signals does not require the signals to be decoded—accordingly, the undecoded, or "raw," signals are used for the summation process. During each timeslot, the sum of all or a substantial portion of the pressure samples collected during that timeslot is computed. The sum value for the timeslot is entered as one element in a length M array, known as the TimeSlotSumArray (TSSA). In a preferred embodiment, this array is initially set to all 0's to ensure well behaved startup. For each resistance computation, the sum of TSSA (i.e., the sum of all pressure samples over the past M timeslots) is updated and used for the resistance computation.

Figure 14:
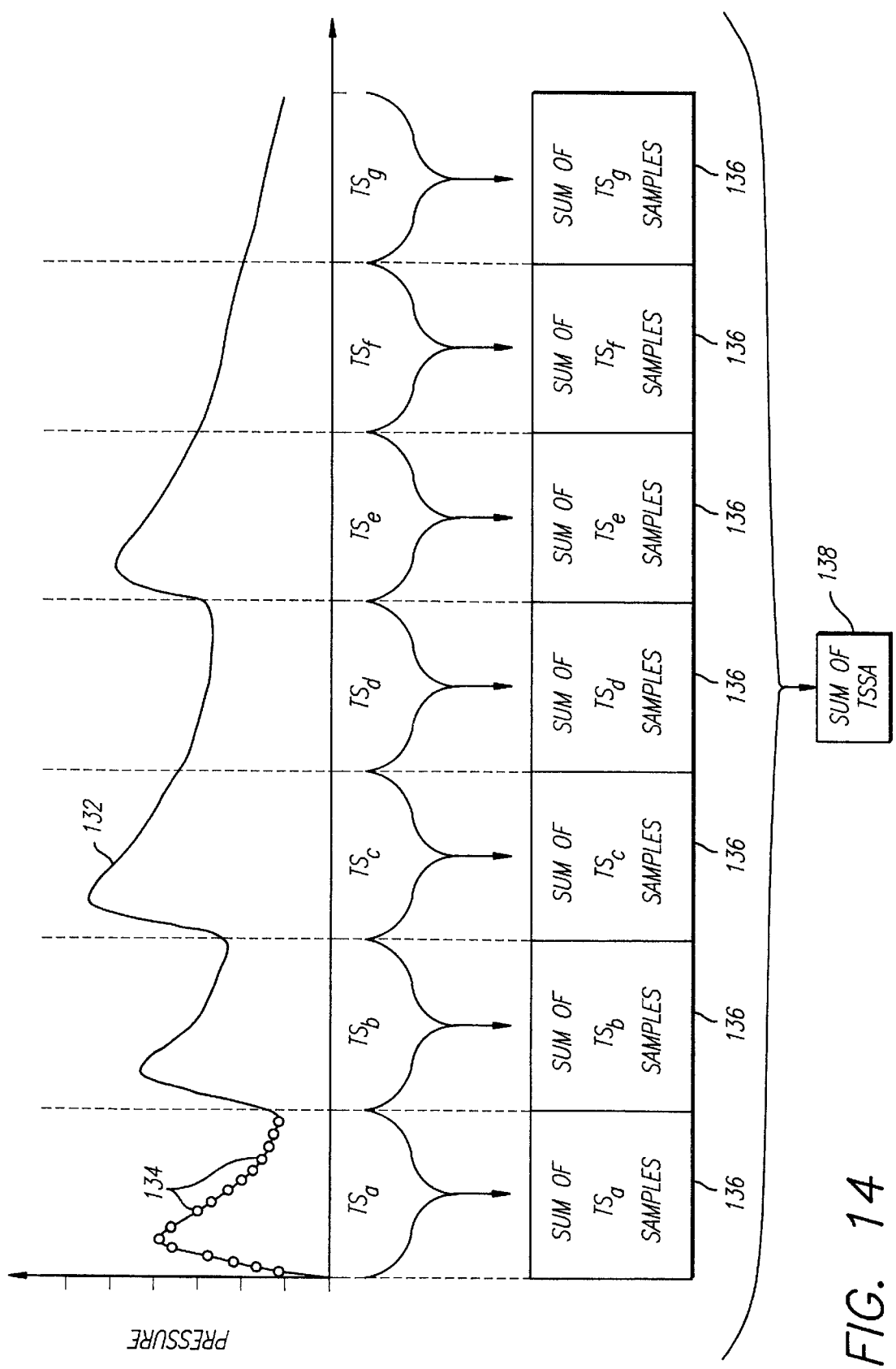
FIG. 14 is a graphical representation of a pressure waveform and corresponding timeslot sum array.

FIG. 14 shows a sample TSSA having a length of 7, corresponding to a PRBS codelength (M) of 7, used to determine a pressure summation for a corresponding undecoded pressure waveform 132. Each timeslot has a plurality of undecoded pressure samples 134 that define the pressure waveform. Each element 136 of the TSSA is used to store the sum of the undecoded pressure samples 134 from a particular timeslot. All elements of the TSSA are then added together to determine an pressure summation 138.

Note that the TSSA is preferably used to keep a moving or running total of the pressure sums for the most recent timeslots. In other words, the TSSA is updated each time that pressure signals from a new timeslot are received, with the data from the "oldest" timeslot being replaced by the new data.

Once the pressure summation and $P_o$ are known, resistance can be computed as:

$$R = \frac{277.77 * \sum_{j=0}^{M-1} TimeSlotSumArray_j - P_oest. \sum_{j=0}^{M-1} SampleSum_j}{SamplesPerSec * SuperstepsPerTimeslot * \frac{\mu l}{Superstep}}$$

where: R=resistance expressed in fluid ohms,
P=pressure in mm Hg, and
277.77 converts mm Hg sec/$\mu$liter to fluid ohms (i.e., mm Hg hour/liter).

It is critical that the value of $\Sigma SampleSum_j$ be identical to the total number of pressure samples contributing to $\Sigma TimeSlotSumArray_j$.

For each timeslot, a new resistance estimate is calculated. However, spurious signals and other transient anomalies between timeslots can cause inaccuracies in calculated resistance values. To reduce the impact of these anomalies, the calculated resistance value can be processed with a median filter. Accordingly, each new resistance estimate is entered into a resistance median filter array. The resistance median filter operates similarly to the $P_o$ median filter, producing a filtered resistance value that is generally an accurate estimate of fluid resistance in the system. As was the case with the $P_o$ filter, the median filter determines the median of the resistance estimates in the array, and this median becomes the filtered resistance value. The resistance median filter array has a length that is rate dependent, with values for a preferred embodiment set forth in Table G. The array elements of the filter are preferably initially set to 0 to minimize startup transients. When the user selected rate is changed without stopping the fluid injection system, all filter array elements are initially set with the most recent filtered resistance value. In a preferred embodiment, the filtered resistance value is presented on the display and alarm processing systems.

TABLE G

| Selected Flow Rate (ml/hr) | Resistance Filter Array Length |
|---|---|
| 0.1–0.5 | 4M (16) |
| 0.6–1.4 | 4M (28) |
| 1.5–3.0 | 4M (60) |
| 3.1–6.1 | 3M (45) |
| 6.2–12.4 | 3M (45) |
| 12.5–24.9 | 3M (45) |
| 25.0–49.9 | 3M (93) |

In addition to determining resistance, the system can also determine other flow parameters, including compliance, system impedance, etc. For example, the system could be used to determine a Time Constant TC (which equals Resistance times Compliance) using the following formula:

$$TC = \frac{\int t(P(t) - P_o)dt}{\int (P(t) - P_o)dt}$$

The above reduces to the discrete form:

$$TC = \frac{\sum_{k=1}^{M} k\Delta T(P(k) - P_o)}{\sum_{k=1}^{M} \Delta T(P(k) - P_o)}$$

where:
k=the index range;
ΔT=the timeslot interval (i.e., timeslot length);
M=the number of samples;
P(k)=the M samples from the decoder; and
$P_o$=estimated equilibrium pressure.

Using the above determination of TC in combination with the separately determined resistance (such as the filtered resistance value), system compliance can be easily determined. Because TC=Compliance times Resistance, Compliance can be simply computed as TC divided by R.

An additional benefit of using a pseudorandom code is the ability to discriminate pressure signals caused by other sources of noise, even pressure signals caused by other pumps operating on a common fluid infusion system. In the embodiment depicted in FIG. 17, a fluid infusion system or assembly 150 includes two fluid infusion segments 152a, 152b, each of which comprises a separate fluid source 22a, 22b, separate processors 30a, 30b, separate pump motors 14a, 14b, and separate pump mechanisms 16a, 16b acting on separate fluid lines 12a and 12b. The separate fluid lines 12a and 12b feed into a common fluid line 12c for infusion to a patient 24 through a common cannula 26. Accordingly, the fluid lines of the two systems essentially form a common 25 fluid conduit. Thus, fluid flow induced by pump mechanism 16a causes corresponding pressure responses that are monitored not only at pressure sensor 34a in conduit 12a but also at pressure sensor 34b in conduit 12b. Similarly, fluid flow induced by pump mechanism 16b causes corresponding pressure responses that are monitored not only at pressure sensor 34b in conduit 12b but also at pressure sensor 34a in conduit 12a. Without proper filtering, such pressure response crosstalk can degrade the accuracy of resistance and other measurements.

Pseudorandom coding and decoding inherently filters out such crosstalk, making it possible for each separate infusion segment 152a, 152b to accurately determine flow resistance. For example, infusion segment 152a preferably operates using a pseudorandom code that causes a resulting fluid flow pattern that is distinct from the flow pattern induced by infusion segment 152b. By decoding the resulting pressure response in accordance with the pseudorandom code, the processor 30a of infusion segment 152a inherently filters out much of the crosstalk caused by infusion segment 152b. Accordingly, resistance can be determined with relative accuracy. Accuracy can be further enhanced by applying the median filter technique shown in FIG. 11. Thus, the individual processor 30a, 30b of each of the infusion segments 152a, 152b can individually determine resistance by filtering the monitored pressure signals with the pseudorandom code used by the particular processor 30a, 30b to generate fluid flow with the respective pump mechanism 16a, 16b.

Figure 17:
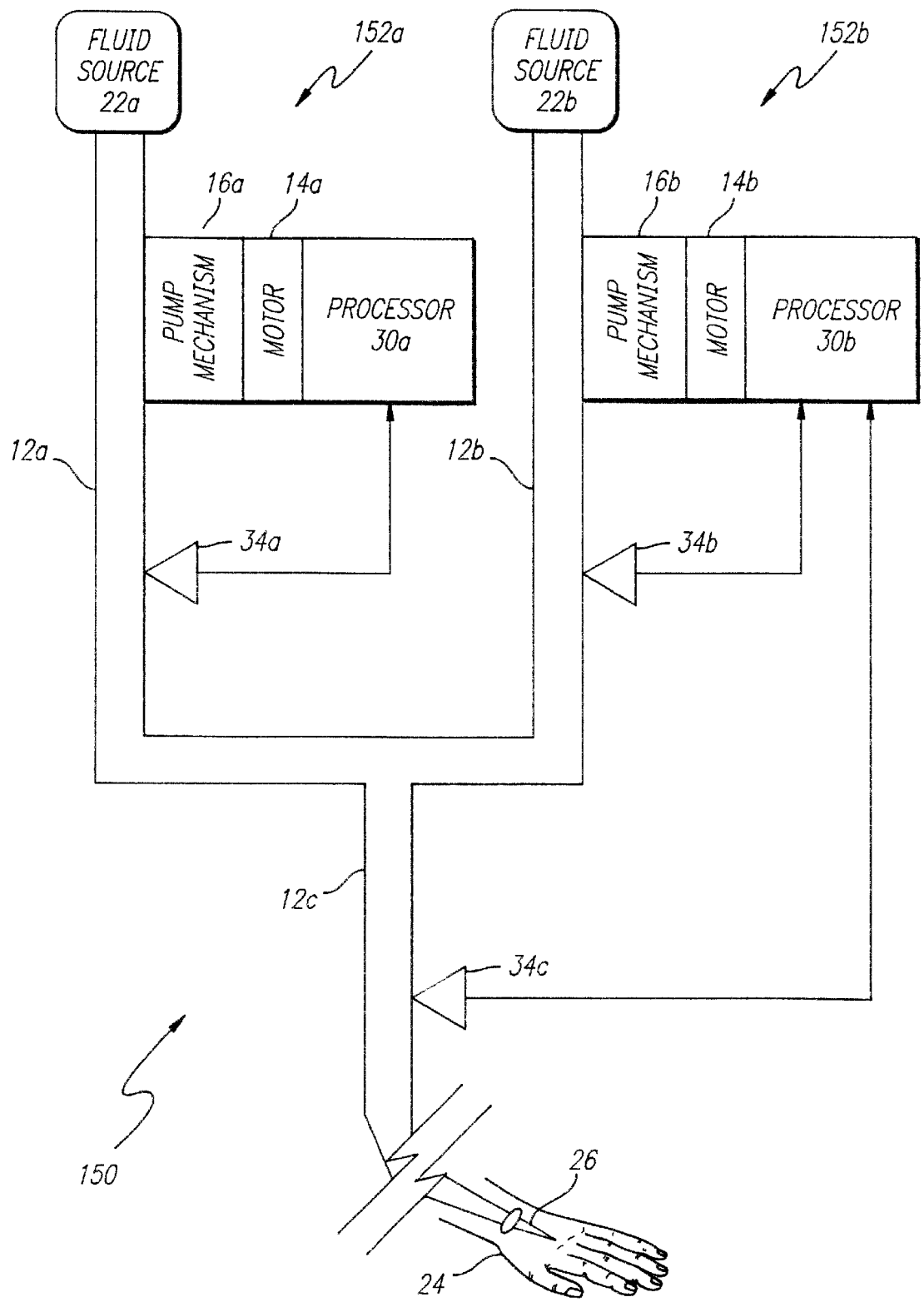
FIG. 17 is a simplified diagram showing a system for monitoring resistance in a fluid infusion system having two fluid infusion segments.

FIG. 17 shows both of the infusion segments 152a, 152b as having processor-controlled infusion mechanisms. In one embodiment, each processor 30a, 30b controls fluid flow in accordance with a pseudorandom code. This further enhances the ability of each processor to filter out crosstalk from the opposing infusion segment. However, if both processors 30a, 30b were using the same pseudorandom code, the ability of the coding/decoding process to filter out crosstalk would be seriously degraded. Additionally, there are certain pairings of pseudorandom codes that, when each is used in a separate infusion segment (such as 152a, 152b), can degrade or enhance the ability of the coding/decoding process to filter out crosstalk. Accordingly, in a further embodiment, the processors 30a, 30b cooperate to ensure that each infusion segment 152a, 152b is infusing fluid in accordance with a different pseudorandom code than the other infusion segment. The processors may further cooperate to select pseudorandom codes that enhance each processors ability to filter out the crosstalk created by the other infusion segment. For example, the processors 30a, 30b may purposefully select different Octal codes that generate PRBS codes which enhance the ability of the processors 30a, 30b to filter out the crosstalk via the coding/decoding process. In another embodiment, the separate infusion segments 152a, 152b may be controlled by a single processor the coordinates the pseudorandom coding used to drive each pump mechanism 16a, 16b.

In the embodiment depicted in FIG. 17, both infusions segments 152a, 152b include a processor 30a, 30b that controls fluid infusion. However, resistance can be determined where only one of the infusion segments includes a processor that controls fluid infusion according to a pseudorandom code. For example, if infusion segment 152a was a conventional infusion device that did not operate according to a pseudorandom code, infusion segment 152b could still determine a resistance so long as processor 30b used pseudorandom coding and decoding.

The pressure sensor used by a particular processor (such as 30b) does not necessarily have to be positioned in the immediately adjacent fluid conduit (such as conduit 12b). Because pressure responses are often similar throughout the fluid infusion system, the pressure sensor might be positioned almost anywhere in the infusion system that is downstream of the pump mechanisms 16a, 16b. For example, the pressure sensor might be positioned in common conduit 12c, as shown by sensor 34c. Thus, processor 30b could receive the pressure signals provided by sensor 34c, sum and decode those signals, and accurately determine resistance and other parameters of the system.

While FIG. 17 shows two fluid infusion segments 152a, 152b, pseudorandom coding (such as PRBS coding) could be used in infusion systems having three or more fluid infusion segments. Although each additional infusion segment adds additional "noise" or crosstalk to the system, the pseudorandom coding/decoding process can eliminate much of the crosstalk.

The above-cited system and method for medium flow rates, whereby pseudorandom coding and decoding is used with the monitored pressure response, is effective for determining fluid resistances and other parameters over a wide range of flow rates. However, for very low flow rates, the pressure produced is quite small. Consequently, small errors in the $P_o$ estimation can produce large errors in the computed resistance. At extremely low rates, such as those below 0.5 ml/hr, mechanical-coupling induced errors and thermal drift of the pressure transducer can produce very significant errors in a PRBS encoded output, leading to large errors in the computed resistance. Accordingly, an alternate means for resistance computation may be preferable.

Figure 15:
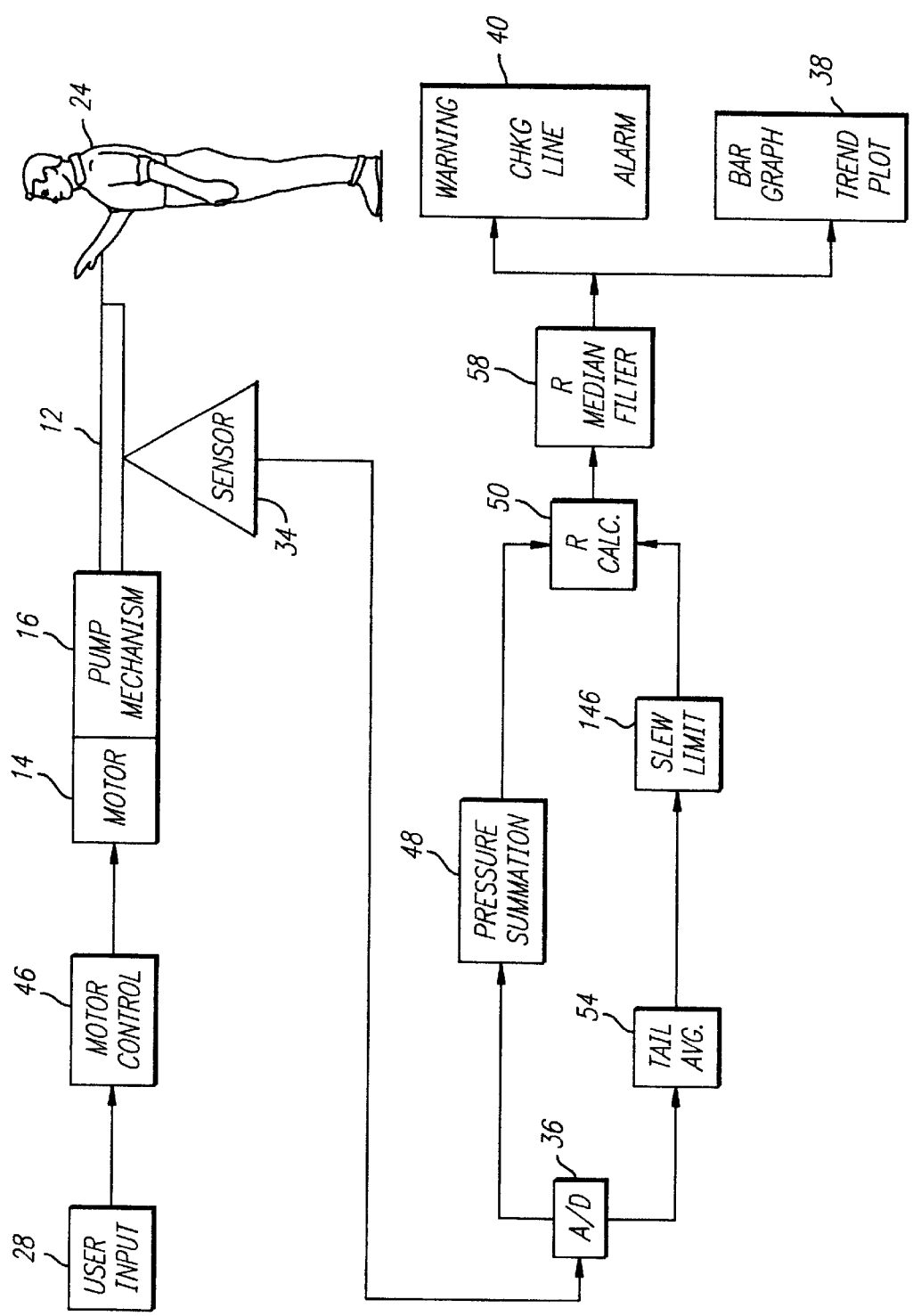
FIG. 15 is a simplified flowchart showing a process for determining resistance according to one embodiment of the invention.

FIG. 15 illustrates a system and method in a preferred embodiment of the invention for determining resistance for very low flow rates, wherein resistance determination is performed on a timeslot by timeslot basis. The drive controller does not use PRBS encoding. Instead, timeslot length is maximized, all timeslot lengths are set to equal values, and each timeslot contains a single Superstep. This allows continually updated resistance estimates to be produced with each timeslot.

In the system for infusing fluid to a patient 24 shown in FIG. 15, the user selects a flow rate at a keyboard or other rate input device 28. The selected rate is then used by the motor controller 46 to determine timeslot length, which is preferably maximized. The motor pump 14 causes the pump mechanism 16 to act on the conduit 12 to deliver one Superstep of fluid in each timeslot, preferably as a single bolus toward the beginning of the timeslot. By maximizing timeslot length, sufficient time is permitted for the monitored pressure to decay to the equilibrium pressure.

The sensor 34 monitors the resulting pressure, and provides pressure signals that are A/D converted 36 and used for pressure summation 48 and tail averaging 54. Tail averaging is performed only over a portion of the timeslot, as shown in FIG. 16.

Figure 16:
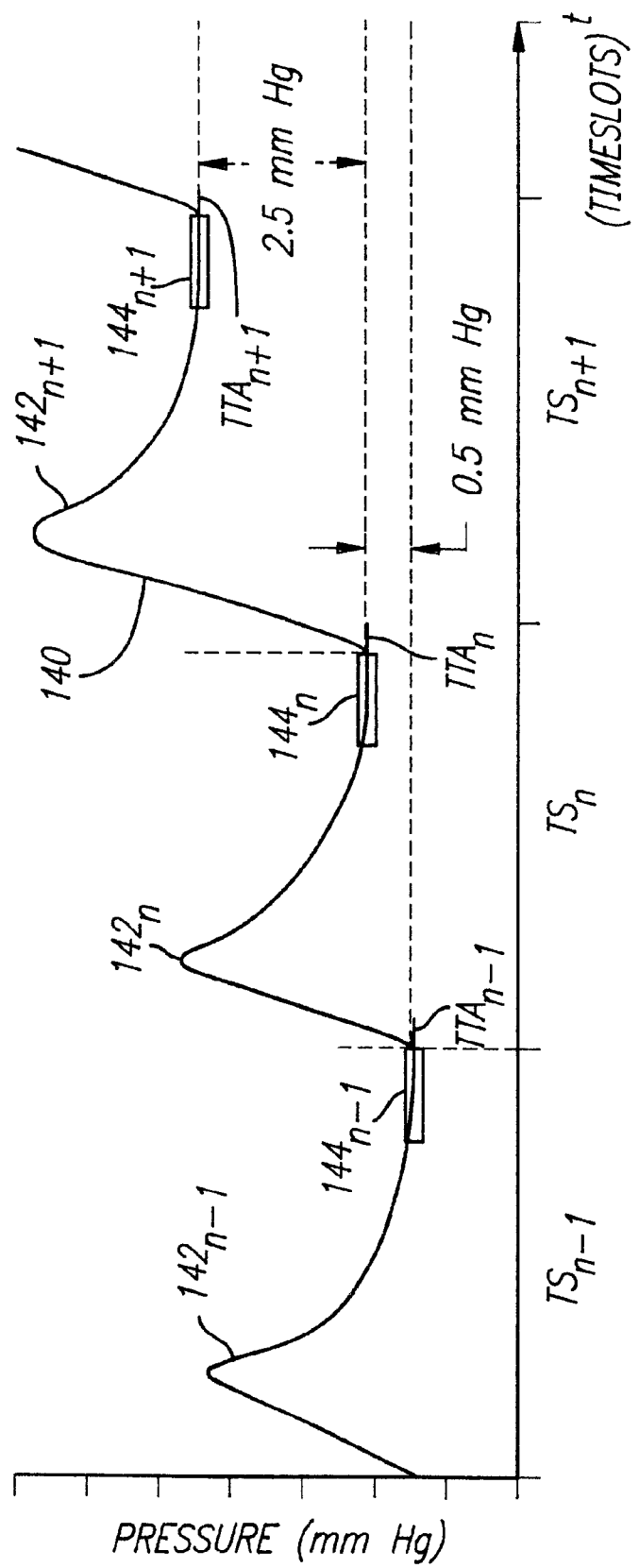
FIG. 16 is a graphical representation of pressure waveforms at very low flow rates.

FIG. 16 illustrates a sample pressure waveform 140 created using the system and method shown in FIG. 15. The resulting pressure waveform 140 is shown for three subsequent timeslots $TS_{n-1}$, $TS_n$, and $TS_{n+1}$. Each timeslot shows an initially increasing pressure wave 142 that decays down to an equilibrium pressure. The last portion of the decaying pressure waveform in the timeslot is known as the tail 144, so that an average taken over this last portion is also known as the Timeslot Tail Average (TTA). The equilibrium pressure $P_o$ is determined as an average of pressures in order to prevent transient pressure anomalies, such as those caused by patient movement, from skewing the determined equilibrium pressure. In the embodiment shown in FIG. 16, the TTA for each timeslot is determined as the average of the monitored pressures over the last 25% of the timeslot.

Referring again to FIG. 15, the TTA is calculated 54 and used in combination with the full sum of pressures over the entire timeslot in fluid resistance calculation 50. In a preferred embodiment, the resistance is determined using the following formula:

$$R = \frac{277.77 * \sum_{j=0}^{Samples/Timeslot-1} Pressure_j - TTA*Samples/Timeslot}{SamplesPerSec * \frac{\mu l}{Superstep}}$$

where: R=resistance expressed in fluid ohms,
P=pressure in mm Hg, and
277.77 converts mm Hg sec/$\mu$liter to fluid ohms (i.e., mm Hg hour/liter).

This technique for determining fluid resistance is generally accurate in detecting soft occlusions and other abnormalities in the fluid delivery system. However, in the case of a hard downstream occlusion, the TTA as well as the other pressure sample values of a timeslot would be elevated by the full amount of pressure developed by the pump's attempt to displace the Superstep of fluid volume into the occluded fluid delivery system. Accordingly, the pressure waveform is often substantially the same between adjacent timeslots, except that the entire waveform is elevated. This is shown in FIG. 16, where the pressure waveform portion in the first timeslot (i.e., $TS_{n-1}$) is substantially the same as the pressure waveforms in the second and third timeslots (i.e., $TS_n$, and $TS_{n-1}$) except for the waveform in each timeslot being slightly elevated over the previous timeslot. Thus, use of just the TTA alone might prevent detection of the occlusion.

To remedy this problem, a threshold value is established to detect relatively large changes in pressure values between adjacent timeslots. In a preferred embodiment, a threshold value or slew limit is determined by adding a selected value to the TTA (i.e., the $P_o$) from the previous timeslot. If the TTA from a timeslot exceeds the slew limit threshold (i.e., exceeds the TTA of the previous timeslot by more than the selected value), a hard occlusion may be indicated. This technique allows for accurate detection of hard occlusions while tracking slow drift (i.e., pressure changes of less than 1 mm Hg/hr which occur due to very slow processes, such as gradual inclusion of moisture, curing of adhesive bonds, migration of implanted ions within the silicon structure, etc.) The technique also avoids errors due to mechanism coupling.

In the embodiment shown in FIG. 16, the selected value added to the previous Timeslot Tail Average to set the slew limit threshold is 2 mm Hg. Pressure increase between adjacent timeslots due to a hard occlusion will generally be much larger than 2 mm Hg, while the magnitude of Superstep to Superstep pressure errors due to mechanical coupling and similar factors is typically less than 2 mm Hg. Accordingly, the system compares the TTA of a timeslot to the TTA of the previous timeslot. If there is an increase of 2 mm Hg or more in the TTA of the more recent timeslot relative to the immediately previous timeslot, then the current $P_o$ value will be limited to the previous TTA+2 mm Hg. Since hard occlusions produce significantly larger pressure increases, the resulting resistance computed from this limited $P_o$ estimate will be very high, indicating a hard occlusion.

By way of example, $TTA_n$ of timeslot $TS_n$ in FIG. 16 is only 0.5 mm Hg greater than $TTA_{n-1}$ of timeslot $TS_{n-1}$. Such an increase is likely due to various error factors, and is not necessarily indicative of a hard occlusion. However, $TTA_{n+1}$ of timeslot $TS_{n+1}$ is 2.5 mm Hg higher than $TTA_n$ of timeslot $TS_n$. Because $TTA_{n+1}$ is more than 2 mm Hg greater than $TTA_n$, the slew limit has been exceeded. As shown in FIG. 15, if slew limit examination 146 determines that there is too great a difference between adjacent TTA values, the current $P_o$ value will be limited to the previous TTA+2 mm Hg. When the limited $P_o$ value is used to determine resistance, a large resistance value will likely result, and the system will activate an occlusion alarm.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. A method for monitoring a flow parameter in a fluid delivery system in which a flow control device acts on a fluid conduit to control the flow of fluid through the conduit, the method comprising the steps of:

outputting a pseudorandom code;

controlling the flow control device to act on the fluid conduit to cause a pattern of flow variation in the conduit in accordance with the pseudorandom code;

monitoring pressure of the fluid in the conduit and generating pressure signals representing said monitored pressure;

determining average pressure values for at least some of the pressure signals;

decoding the average pressure values in accordance with the pseudorandom code; and processing the decoded average pressure values to determine the flow parameter.

2. The method of claim 1, wherein the step of determining a flow parameter includes determining flow resistance.

3. The method of claim 1, comprising the further step of:

processing the decoded averaged pressure values to determine an estimated equilibrium pressure.

4. The method of claim 1, wherein the step of outputting a pseudorandom code comprises outputting a PRBS code.

5. The method of claim 4, wherein the flow control device comprises an infusion pump having a plurality of movement steps per cycle, each step causing a step volume of fluid to flow through the conduit, and the method comprises the further step of:

controlling the infusion pump to group the movement steps into a plurality of supersteps, each superstep causing a superstep volume of fluid to flow through the conduit, with each superstep volume being approximately equal to the other superstep volumes.

6. The method of claim 5, comprising the further step of:

assigning a timeslot having a timeslot length to each element of the PRBS code;

wherein the step of controlling the infusion pump includes controlling the infusion pump to induce at least one superstep volume of fluid to flow in the conduit during each timeslot that has a corresponding PRBS element of 1, and controlling the infusion pump to induce no volume of fluid to flow during each timeslot that has a corresponding PRBS element of 0.

7. The method of claim 6, wherein the step of controlling the infusion pump includes controlling the infusion pump to induce the superstep volume of fluid to flow as a single bolus of fluid delivered at the beginning of the timeslot using an acceleration/deceleration flow waveform.

8. The method of claim 6, wherein the step of controlling the infusion pump includes controlling the infusion pump to induce two or more superstep volumes of fluid to flow in each timeslot as a series of two or more adjacent fluid boluses delivered at the beginning of the timeslot, with each of said adjacent fluid boluses delivered in accordance with an acceleration/deceleration waveform.

9. The method of claim 6, comprising the further steps of:

selecting a flow rate; and determining the timeslot length and associated superstep volume in accordance with the selected flow rate to produce the selected flow rate.

10. A system for infusing fluid to a patient through a conduit, the system comprising:

an infusion pump acting on the conduit and having a plurality of movement steps per cycle, each step causing a step volume of fluid to flow through the conduit; and a pressure sensor coupled to the conduit for providing pressure signals in response to pressure sensed in the conduit;

a processor configured to output a PRBS code having a codelength and a plurality of elements, assign a timeslot to each element of the PRBS code, control the flow control device to act on the conduit to cause flow in the conduit in a pattern of flow variation in accordance with the PRBS code, receive the pressure signals, determine average pressure values for at least some of the pressure signals, decode the average pressure values in accordance with the PRBS code, and process the decoded average pressure values to determine a flow parameter.

11. The system of claim 10, wherein the processor is configured to control the infusion pump to group the pump movement steps into a plurality of supersteps, each superstep causing a superstep volume of fluid to flow through the conduit, with each superstep volume being approximately equal to the other superstep volumes.

12. The system of claim 11, wherein one or more of the timeslots are active timeslots, and the processor is configured to control the infusion pump to induce at least one superstep volume of fluid to flow in the conduit at the beginning of each active timeslot.

13. The system of claim 12, wherein the processor is configured to determine average pressure values for at least some of the pressure signals from the tail portion in each active timeslot.

14. A system for infusing fluid to a patient through a conduit, the system comprising:

a first infusion device acting on a first segment of the conduit;

a pressure sensor coupled to the conduit and providing pressure signals in response to fluid pressure sensed in the conduit;

a processor configured to output a first pseudorandom code having a codelength, control the first infusion device to act on the first segment of the conduit to cause fluid flow in accordance with the first pseudorandom code, receive the pressure signals, determine average pressure values for at least some of the pressure signals, decode the average pressure signals in accordance with the first pseudorandom code to create first decoded average pressure values, and process the first decoded average pressure values to determine a first flow parameter; and a second infusion device acting on a second segment of the conduit.

15. The system of claim 14, wherein the first segment and second segment are separate branches of the conduit that are joined at a point downstream of both the first and second infusion devices.

16. The system of claim 14, wherein the processor is configured to output a second pseudorandom code having a codelength, and control the second infusion device to act on the conduit to cause flow in accordance with the second pseudorandom code.

17. The system of claim 16, wherein processor is configured to select a second pseudorandom code that is different from the first pseudorandom code.

18. The system of claim 17, wherein the processor is configured to select first and second pseudorandom codes that enhance the ability of the processor to filter out crosstalk from the second infusion device.

19. The system of claim 16, wherein the processor is configured to decode the average pressure signals in accordance with the second pseudorandom code to create second decoded average pressure values, and process the second decoded average pressure values to determine a second flow parameter.

20. A method for monitoring at least one flow parameter in a fluid conduit in which a first infusion device acts on a first fluid conduit segment, and a second infusion device acts on a second fluid conduit segment to control the flow of fluid through the conduit, the method comprising the steps of:

providing pressure signals in response to fluid pressure sensed in the conduit;

outputting a first pseudorandom code having a codelength;

controlling the first infusion device to infuse fluid in a pattern of flow variation in accordance with the first pseudorandom code;

monitoring pressure of the fluid in the conduit and generating pressure signals representing said monitored pressure;

determining average pressure values for at least some of the pressure signals;

decoding the average pressure values in accordance with the first pseudorandom code to create first decoded average pressure values; and processing the first decoded average pressure values to determine a first flow parameter.

21. The method of claim 20, comprising the further steps of:

outputting a second pseudorandom code having a codelength;

controlling the second infusion device to infuse fluid in a pattern of flow variation in accordance with the second pseudorandom code.

22. The method of claim 21, wherein the step of outputting the second pseudorandom code includes the step of selecting the second pseudorandom code to enhance the ability of the processor to filter out crosstalk from the second infusion device.

23. The method of claim 21, comprising the further steps of:

decoding the average pressure values in accordance with the second pseudorandom code to create second decoded average pressure values; and processing the second decoded average pressure values to determine a second flow parameter.

* * * * *

UNITED STATES PATENT AND TRADEMARK OFFICE
CERTIFICATE OF CORRECTION

PATENT NO. : 6,416,291 B1
DATED : July 9, 2002
INVENTOR(S) : Robert D. Butterfield et al.

It is certified that error appears in the above-identified patent and that said Letters Patent is hereby corrected as shown below:

<u>Column 6,</u>
Line 32, change "high", to read -- low --.

Signed and Sealed this

Fifth Day of November, 2002

*Attest:*

JAMES E. ROGAN
*Attesting Officer*     *Director of the United States Patent and Trademark Office*